United States Patent [19]

von Sprecher et al.

[11] Patent Number: 4,649,215
[45] Date of Patent: Mar. 10, 1987

[54] ALIPHATIC THIOETHERS

[75] Inventors: Andreas von Sprecher, Oberwil; Ivan Ernest, Birsfelden, both of Switzerland; Alan J. Main, Chatham Township, Morris County, N.J.; Andreas Beck, Freiburg, Fed. Rep. of Germany

[73] Assignee: Ciba-Geigy Corporation, Ardsley, N.Y.

[21] Appl. No.: 748,656

[22] Filed: Jun. 25, 1985

[30] Foreign Application Priority Data

Jun. 28, 1984 [CH] Switzerland ............... 3115/84
Feb. 12, 1985 [CH] Switzerland ............... 617/85

[51] Int. Cl.$^4$ ............... C07C 149/20; C07C 147/02
[52] U.S. Cl. ............... 560/152; 560/153; 562/556; 562/581
[58] Field of Search ............... 560/152, 153; 562/556, 562/557, 581

[56] References Cited

FOREIGN PATENT DOCUMENTS 0068739 5/1983 European Pat. Off. .

OTHER PUBLICATIONS

Biochem. and Biophys. Res. Commun., vol. 117, No. 3 (1983), 732-739.
Chem. Pharm. Bull., vol. 30, (1982), 2453-2462.
Chem. Pharm. Bull., vol. 31, (1983), 3326-3329.
Proc. Nat'l Acad. Sci., vol. 78, (1981), 3195-3198.
Chem. Abstr., vol. 104, (1986), 62811.
Chem. Abstr., vol. 101, (1984), 164384.
Chem. Abstr., vol. 102, (1985), 143319.
Chem. Abstr., vol. 102, (1985), 166532.
Chem. Abstr., vol. 102, (1985), 179763.
Chem. Abstr., vol. 102, (1985), 179833.
Chem. Abstr., vol. 103, (1985), 172911.
Chem. Abstr., vol. 103, (1985), 65702.

*Primary Examiner*—Delbert R. Phillips
*Attorney, Agent, or Firm*—Michael W. Glynn; Irving M. Fishman

[57] ABSTRACT

Novel asymmetric thioethers of the formula

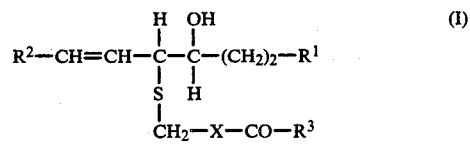

in which $R^1$ represents a $C_{1-3}$-alkyl radical or a $C_{1-3}$-hydroxyalkyl radical of which the hydroxy group may be in esterified form, $R^2$ represents an optionally unsaturated aliphatic radical having from 5 to 15 carbon atoms, $R^3$ represents hydroxy, alkoxy or an optionally substituted amino group, and -X- represents a single bond, a methylene group or an optionally N-acylated primary aminomethylene group wherein the O-atom of the hydroxy group is in the transconfiguration relative to the S-atom, are effective as leucotriene-antagonists since they eliminate the contractions of smooth muscles caused by leucotrienes and are therefore suitable for the treatment of allergic, especially asthmatic, conditions.

36 Claims, No Drawings

ALIPHATIC THIOETHERS

The invention relates to novel asymmetric aliphatic thioethers derived from the residue (A) of a mercaptoalkanecarboxylic acid, such as mercaptoacetic acid or β-mercaptopropionic acid, of a cysteine or cysteine peptide optionally acylated at the nitrogen atom, or of a salt or of a derivative, modified at the carboxyl group, of such an acid, the sulphur atom of which is substituted by an olefinic radical (B) having at least 12 carbon atoms, which radical carries on one side of its chain, in the α-position to the sulphur atom, a hydroxy group that is trans-orientated in relation to the S-atom, and on the other side a double bond.

The invention relates especially to compounds of the formula

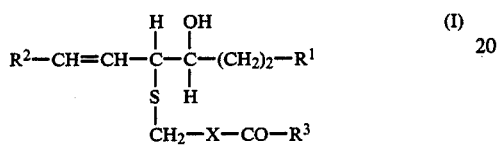

in which
- $R_1$ represents a $C_{1-3}$-alkyl radical or a $C_{1-3}$-hydroxyalkyl radical of which the hydroxy group may be in esterified form,
- $R^2$ represents an optionally unsaturated aliphatic radical having from 5 to 15 carbon atoms,
- $R^3$ represents hydroxy, alkoxy or an optionally substituted amino group, and
- —X— represents a single bond, a methylene group or an optionally N-acylated primary aminomethylene group wherein the O-atom of the hydroxy group is in the trans-configuration relative to the S-atom, and to salts of such compounds having salt-forming properties.

The spatial representation in the above formula I is to be understood as follows: the symbols of the first line lie above, and those of the third line therefore below, the plane of representation (or vice-versa), which for the formula shown corresponds to the opposite configuration (RS)-(SR) of both central carbon atoms according to the Kahn-Ingold-Prelog convention.

The invention relates also to processes for the manufacture of the above-defined compounds according to the invention, and to pharmaceutical compositions that contain these compounds as active ingredient, and to corresponding manufacturing processes by which such compositions are manufactured by non-chemical methods. The invention relates furthermore to the therapeutic use of the above-defined compounds and pharmaceutical compositions, especially in alleviating and curing those pathological conditions in which the pronounced leucotriene-antagonistic activity of the compounds according to the invention can be utilized, such as in the case of allergies of various types, especially in the case of asthma.

A few years ago it was discovered that isolates from biological material of various origins known from immunological studies (cf. H.R. Morris et al. Nature 285, 1045-106 (May 1980) and L. Oerning, S. Hammarström and B. Samuelsson: Proc. Natl. Acad. Sci. USA 77 (4), 2014-2017 (1980)) as SRS (slow-reacting substance of anaphylaxis), are identical to the so-called leucotrienes known from the study of the arachidonic acid metabolism. It is thus clear, for example from the two last-mentioned works, that the active substance referred to as SRS-A, which, as a primary cause of the immediate onset of hypersensitivity reactions, is in all probability responsible for bronchial constriction in asthma, is identical to so-called leucotriene D (cf. the following formula LTD). Leucotriene C, the spatial structure of which has also recently been confirmed [E.J. Corey et al., J.Am. Chem. Soc. 102 (4), 1436-1439 (1980)]by total synthesis, has a similar action.

The basic structural framework of leucotrienes in general is formed by a polyunsaturated linear icosanic acid which carries characteristic substituents in the 1-, 5- and 6-positions, as is shown by the formula below for the mentioned most important representatives:

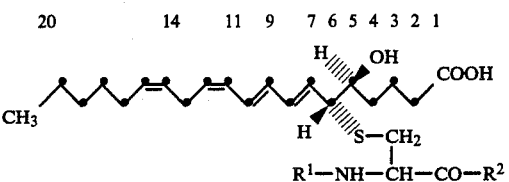

LTC-4: $R^1$=HOCOCH(NH$_2$)CH$_2$CH$_2$CO- ; $R^2$=-NHCH$_2$COOH
LTD-4: $R^1$=H- ; $R^2$=-NHCH$_2$COOH
LTE-4: $R^1$=H- ; $R^2$=-OH

[Here, the spatial representation is to be understood as follows: the entire olefinic chain lies in the plane of representation and the valency lines indicated by arrows extend above the plane of representation whilst the broken lines extend below the plane.]

In their physiological properties, leucotrienes are in general distinguished by the fact that they cause a marked contraction of smooth muscle of the most varied kinds. From the standpoint of health such an effect is generally undesirable, and accordingly the search for suitable leucotriene antagonists is in the forefront of research in this field.

Surprisingly, it has now been shown that although the compounds of the formula I according to the invention have several structural features in common with known leucotrienes, they have a pronounced antagonistic effect on the latter. Thus, in various test arrangements in vitro they have a clear leucotriene-antagonistic action.

For example, in the tested concentration range of approximately from 0.1 to 25 μmol/l they inhibit the contraction of a smooth muscle induced by leucotriene-D$_4$ (LTD$_4$ - see above). This so-called LTD$_4$-antagonism is demonstrated experimentally, for example, in the following manner: In segments taken from the ileum of a guinea pig weighing 300-400 g and incubated in an organ bath in Tyrode's solution at 38° C. whilst gassing with a mixture of 95% oxygen and 5% carbon dioxide at a load of 1 g, contractions are triggered with synthetic leucotriene-D$_4$ (in the form of a potassium salt) and isotonically registered. The extent of inhibition by the test substance is ascertained after a preliminary incubation of 2 minutes and evaluated as IC$_{50}$, that is to say the concentration that reduces the test contraction by 50%. The LTD$_4$ -antagonism can also be demonstrated in vivo by a bronchoconstriction standard test on guinea pigs with aerosol administration. (The description of the test method is appended after the Examples).

In another test arrangement, compounds of the formula I, in the tested concentration range of approximately from 1 to 100 μmol/l, inhibit the aggregation of peritoneal leucocytes in rats induced by leucotriene B$_4$ (LTB$_4$). In the experiment, Wistar rats (400–600 g) are sacrificed 24 hours after i.p. injection of 16 ml of 12% sodium caseinate solution, cells are washed from the peritoneum with buffered Eagles minimal essential medium (E-MEM), and 0.5 ml of cell suspension in each case (10$^7$ cells in 1 ml of E-MEM) is placed in the vessel of a platelet aggregometer and heated at 37° C. with constant stirring (800–900 revs/min). Four minutes after the addition of the test substance (2 μl), aggregation is triggered by 2 μl of LTB$_4$ (1 ng/ml final concentration) and continuously registered. The concentration of the test substance that reduces the control aggregation (LTB4 alone) by 50% is designated IC$_{50}$.

Surprisingly, compounds of the formula I also have a pronounced inhibiting effect on other physiologically important enzyme systems. For example, the inhibition of phospholipase A$^2$ from human leucocytes was observed in the tested concentration range of approximately from 0.5 to 50 μmol/l. (The experimental arrangement for this determination is described in detail in the appendix after the Examples.) Similarly, the inhibition of phospholipase C from human thrombocytes was observed in the tested concentration range of approximately from 1 to 100 μmol/l (for the experimental arrangement see the appendix after the Examples).

The antiallergic and antiinflammatory properties indicated in vitro by these methods are also confirmed in animal tests in vivo. For example, the local antiinflammatory activity can be demonstrated, for example, according to the method developed by G. Tonelli and L. Thibault [Endocrinology 77, 625 (1965)], by inhibition of the oedema induced by croton oil in the ears of normal rats in a dosage range of from approximately 1 to approximately 100 mg/ml.

Owing to these valuable pharmacological properties, the compounds of the formula I according to the invention can be used therapeutically in all cases where the allergogenic action of leucotrienes leads to pathological conditions and is to be reduced or eliminated. Consequently, they can be used, for example, for the treatment of allergic conditions and diseases, such as, especially, asthma, but also hay fever and obstructive lung diseases, including cystic fibrosis. Similarly, owing to their antiinflammatory activity, they are suitable as inflammation-inhibiting agents, especially as external (topical) skin antiphlogistic agents for the treatment of inflammatory dermatoses of any kind, such as in the case of mild skin irritations, contact dermatitis, exanthema and burns, and as mucosa anti-phlogistic agents for the treatment of inflammations of the mucosa, for example the eyes, nose, lips, mouth and genital or anal region. They can also be used as sun-screening agents. In addition, the high inhibiting activity on various blood factors suggests the possibility of therapeutic use of the compounds of the formula I in the thrombosis and blood coagulation indication range.

As already mentioned above, there is a general analogy between the structure of the compounds of the formula I according to the invention and that of leucotrienes, especially in the obligatory trans-configuration of the vicinal S- and O-atoms mentioned at the beginning and the total structure of the mercaptoalkanoic acid residue (A) (especially in its typical form of a cysteine peptide). They differ from leucotrienes essentially in lacking the characteristic terminal carboxy group in the olefinic radical (B). Also in contrast to leucotrienes, the number, character and spatial arrangement of the multiple bonds and the total length of the olefinic radical (B) are, within wide limits, incidental to the activity, and even the absolute configuration at both of the above-discussed asymmetric carbon atoms is not critical for the activity, as can be demonstrated using the highly active sodium salt of N-[S-5(R),6(S)-5-hydroxy-7,9-trans-11-cis-icosatrien-6-yl-N-trifluoroacetylcysteinyl]-glycine as an example, which by comparison with natural leucotrienes has reverse absolute configuration of the carbon atoms 5 and 6 of the hydrocarbon chain.

In the above-defined formula I, the symbol R$^1$ preferably represents an alkyl group, such as methyl, propyl and, especially, ethyl, or a corresponding hydroxyalkyl group, preferably ω-hydroxyalkyl, such as, especially, β-hydroxyethyl, wherein the hydroxy group may be present not only in free form but also in esterified form. An esterified hydroxy group is preferably esterified by the radical of an aliphatic or aromatic carboxylic acid having a maximum of 12 carbon atoms, such as benzoic acid or, especially, a C$_{1-7}$-alkanoic acid, especially acetic acid.

The aliphatic radical represented by the symbol R$^2$ is preferably a linear radical, for example an alkyl radical, consisting of from 5 to 15, preferably from 7 to 12, carbon atoms, such as, especially, heptyl, nonyl, undecyl and dodecyl, or a corresponding singly or polyunsaturated radical that carries one, two or three multiple bonds, such as triple bonds and, especially, double bonds, in the cis- or transconfiguration as desired, in any combination. These multiple bonds are preferably as close as possible to the sulphur atom, that is to say conjugated with the first double bond, which is in the α,β-position to the sulphur-carrying carbon atom. Preferred radicals R$^2$ of this type are, for example, 1-alkenyl, 1,3-alkadienyl and 1,3,6-alkatrienyl radicals, such as, especially, 1-heptenyl, 1-octenyl, 1-nonenyl, 1-decenyl, 1-undecenyl and 1-dodecenyl or 1,3-octadienyl, 1,3-decadienyl, 1,3-dodecadienyl and 1,3,6-dodecatrienyl, in which all of the double bonds can each individually be in cis- or trans-configuration and can form any combination.

The symbol R$^3$ defined in formula I given at the beginning forms, together with the adjacent carbonyl group —CO—, a free or functionally modified carboxy group; if R$^3$ represents hydroxy, it forms with the carbonyl group the carboxy group of a free carboxylic acid; if R$^3$ represents an alkoxy group, especially one with a maximum of 7 carbon atoms, especially methoxy, it completes a carboxylic acid ester; and, if R$^3$ represents an amino group, it belongs to the amide bond of a carboxamide or, if the amino group is suitably substituted, of a peptide. In that latter case, the substituted amino group is the base element of an amino acid, such as of an α-aminocarboxylic acid and especially of an α-amino-C$_{2-7}$-alkanoic acid, preferably one that occurs naturally, such as leucine, valine, alanine (especially in the "natural" L form) and, especially, glycine. The carboxy group of those amino acids can then in turn be in the form of free carboxy, or may be functionally modified in the abovedefined manner as an ester group, such as, especially, a C$_{1-7}$-alkoxycarbonyl, or the carboxamide group —COHN$_2$. Such preferred meanings of the symbol R$^3$ thus correspond to the partial formula

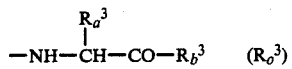

in which $R_a{}^3$ represents a $C_{1-5}$-alkyl group or, preferably, hydrogen, and $R_b{}^3$ represents hydroxy, $C_{1-7}$-alkoxy or the primary amino group $NH_2$.

The initially defined symbol —X— can, on the one hand, represent a single C-C bond, and thus together with the adjacent groups form the residue of mercaptoacetic acid —S—$CH_2$—CO—$R^3$; in this case, of the above-mentioned meanings for $R^3$ hydroxy is especially preferred. On the other hand, —X— can represent an aminomethylene group optionally acylated at the nitrogen atom, which group thus corresponds to the partial formula

in which $R^4$ represents hydrogen or the acyl radical of a carboxylic acid, such as an aliphatic or aromatic carboxylic acid with a maximum of 12 carbon atoms, especially an unsubstituted or substituted, preferably linear, $C_{1-5}$-alkanoic acid. Of substituted alkanoic acids of this kind the following, especially, may be mentioned: on the one hand mono- or, preferably, polyhalogenated, especially chlorinated or fluorinated, $C_{1-5}$-alkanoic acids, such as, especially, trifluoroacetic acid, and, on the other hand, mono- and di-basic amino acids including monoamides of the latter, especially α-amino acids of the type that occur naturally as building blocks of peptides and especially in L-form; of these attention is drawn, for example, to glutamic acid, which preferably acylates the amino group with its γ-carboxy. According to this representation the symbol $R^4$ preferably represents hydrogen, trifluoroacetyl or γ-glutamyl of the formula $HOCOCH(NH_2)CH_2CH_2CO$—, wherein in the latter the free carboxy group may be in the form of a salt.

Preferably, the above-characterised aminomethylene group, together with the adjacent symbols, forms an optionally acylated cysteine residue of the partial formula

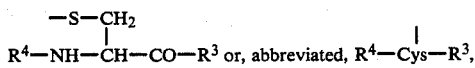

in which $R^3$ and $R^4$ have the above-mentioned general and preferred meanings, wherein the L-cysteinyl residue with the naturally occurring configuration at the asymmetric carbon atom is preferred. In this case $R^3$ preferably represents hydroxy, $C_{1-4}$-alkoxy or a glycine residue bonded at the nitrogen atom and optionally esterified by a $C_{1-4}$-alkanol, and $R^4$ represents especially hydrogen, trifluoroacetyl or γ-glutamyl (also in salt form).

Most of the compounds of the formula I, depending on their individual character, can also be in the form of salts. Those that have adequate acidity, such as especially those with free carboxy groups, can form salts with bases, such as, especially, inorganic bases, preferably physiologically tolerable alkali metal salts, especially sodium and potassium salts. Those of the compounds of the formula I that have adequate basicity, such as esters and amides of amino acids, can be in the form of acid addition salts, especially physiologically tolerable salts, with customary pharmaceutically acceptable acids; of the inorganic acids there may be mentioned especially hydrohalic acids, such as hydrochloric acid, and sulphuric and phosphoric or pyrophosphoric acid, and of the organic acids there may be mentioned especially sulphonic acids, for example aromatic sulphonic acids, such as benzene- or p-toluene-sulphonic acid, embonic acid and sulphanilic acid, or lower alkanesulphonic acids, such as methanesulphonic, ethanesulphonic, hydroxyethanesulphonic acid and ethylenedisulphonic acid, but also aliphatic, alicyclic, aromatic or heterocyclic carboxylic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic and p-aminosalicylic acid, as well as ascorbic acid. Compounds of the formula I that contain both basic and acidic functional groups, such as free carboxy and amino groups, can also be in the form of internal salts.

Attention is drawn in particular to compounds of the formula I in which the entire residue (A) of the mercaptoalkanecarboxylic acid mentioned at the beginning is represented by one of the following formulae, wherein the amino acid residues of the "natural" L-series are preferred:

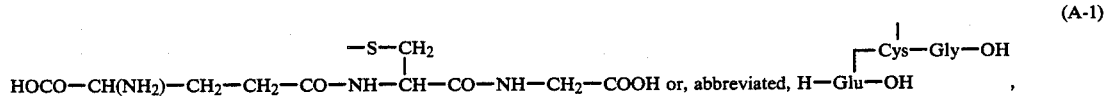

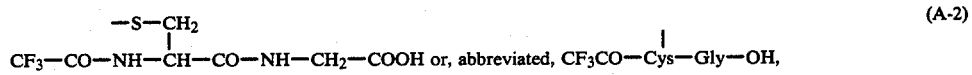

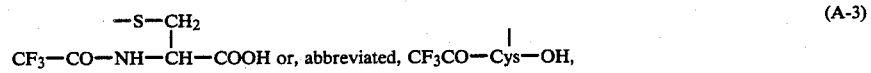

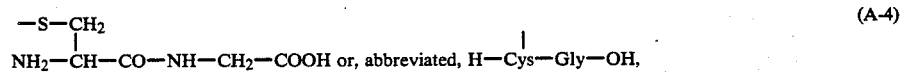

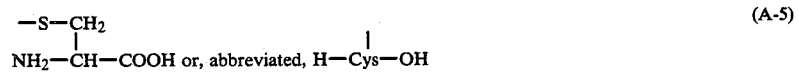

and $$-S-CH_2-COOH. \quad (A-6)$$

Also included are corresponding compounds in which the carboxy groups are present in the form of a primary amide or $C_{1-4}$-alkyl ester, or especially in the form of a salt, preferably an alkali metal salt.

Attention is drawn more especially to the compounds of the formula I described in the Examples.

The thioethers according to the invention can be manufactured in a manner known per se, for example in the following manner: an unsaturated aliphatic trans-epoxide having a minimum of 12 carbon atoms and corresponding to the radical (B) defined at the beginning, which carries a double bond at least in the α-position to the epoxy group, especially of the formula

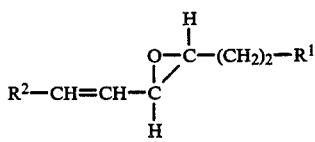
(II)

in which $R^1$ and $R^2$ have the meanings given above and the two hydrogen atoms at the oxirane ring are trans-orientated with respect to one another, and in which a hydroxy group, if present, can be in a protected form, is reacted with a mercaptoalkanecarboxylic acid corresponding to the above-defined residue (A), especially one of the formula $$HS-CH_2-X-CO-R^3 \quad (III)$$

in which $R^3$ and $-X-$ have the meanings given above, in which acid an amino group, if present, can be in protected form, or with a salt thereof or a derivative thereof with a modified carboxy group, and, if necessary or desired, the protecting groups of the hydroxy and/or amino group are removed and/or a compound present in the form of an ester is hydrolysed to the free acid or a salt thereof, and, if desired, a resulting free compound with salt-forming properties is converted into a salt thereof or a resulting salt is converted into a free compound.

The reaction is carried out under conditions known per se at temperatures of from approximately −20° C. to approximately +50° C., preferably at room temperature, and especially in a basic medium, for example in the presence of an amine, especially a tertiary aliphatic, arylaliphatic or saturated heterocyclic amine, such as trialkylamine (for example triethylamine, or ethyldiisopropylamine), dialkylbenzylamine (for example N,N-dimethylbenzylamine), N,N-dialkylaniline (for example N,N-dimethylaniline) or N-methyl- or N-ethyl-piperidine or N,N'-dimethylpiperazine. Usually, the reaction is carried out in an organic solvent, such as a lower alkanol, for example methanol or ethanol, which is inert under the reaction conditions.

If a free hydroxy group is present in the starting material, especially in the substituent $R^1$ of the formula II, it can be present in a protected, such as etherified, form during the reaction. Preferred are readily removable, especially acidolytically removable, hydroxy-protecting groups, such as are generally well known, especially from peptide and steroid chemistry; of these, protecting groups of the tert.butyl ether type and, especially, tetrahydropyranyl ether (THP ether) are especially preferred. When the main reaction (that is to say condensation of the epoxide with the mercaptocarboxylic acid) is complete, these protecting groups can be removed in generally known manner to free the hydroxy group, for example by treatment with an organic acid, such as formic acid, acetic acid, oxalic acid or trifluoroacetic acid, or a mixture thereof, and optionally in the presence of water and/or inert organic solvents, such as lower alkanols (for example methanol or ethanol) and cyclic ethers (such as tetrahydrofuran or dioxan).

If the mercaptocarboxylic acids used as starting material contain a free amino group, then this can preferably be in a protected, such as especially an acylated, form during the main reaction. Preferably, readily removable, especially acidolytically removable, amino-protecting groups are used, such as, together with conditions for their removal, are generally well known, especially in peptide chemistry. Of the amino-protecting groups, however, the trifluoroacetyl group is to be given special mention: when the main reaction is complete this can remain in the end product according to the invention or, if desired, can subsequently be removed. The removal of the N-trifluoroacetyl group is carried out, as is known, preferably by hydrolysis, especially under basic conditions, such as with alkali metal carbonates (for example sodium or potassium carbonate) or dilute alkali hydroxide solutions (for example sodium or potassium hydroxide) in the presence of water in a water-miscible organic solvent, such as a lower alkanol (for example methanol or ethanol) or cyclic ether (for example tetrahydrofuran or dioxan) at temperatures of approximately from 0° to 80° C., preferably at a slightly elevated temperature of approximately from 50° to 60° C. If ester groups are present in the product to be hydrolysed, such as an acylated hydroxy group in the hydroxyalkyl radical R1 or an esterified carboxy group in the mercapto acid residue (A), then they are simultaneously hydrolysed under these conditions.

In the main reaction (condensation with epoxide) the mercaptocarboxylic acid is used especially in the form of its ester, preferably a $C_{1-4}$-alkyl ester (such as the methyl or ethyl ester); if the end product according to the invention is desired in the form of a free acid or its salt, then the resulting ester must be hydrolysed. The hydrolysis is carried out under the customary conditions, for example those described hereinbefore for the base-catalysed hydrolytic removal of the N-trifluoroacetyl group. It is, however, also possible selectively to remove the ester group with retention of the N-trifluoroacetyl group under milder conditions, such as especially at lower temperature (preferably at room temperature), with an equivalent stoichiometric amount of alkali, and through a shortened reaction time, optionally with analytical monitoring, for example by thin layer chromatography, but in the course of this an acylated hydroxy group is generally removed at the same time.

Starting materials for the condensation process according to the invention are either known per se or can be obtained in a manner known per se according to known analogy processes. Thus, for example, the important mercaptocarboxylic acids of the formula III have been described (cf. for example, E.J. Corey et al.: Tetrahedron Letters 1980, 3143), and other analogous acids can be obtained in the same manner starting from corresponding known starting materials. For the manufacture of cysteine derivatives, analogous known cystine compounds are advantageously used and subjected to the customary reductive cleavage of the disulphide bond, or are processed like cysteine derivatives with a mercapto group that is suitably protected, for example by trityl or acetylaminomethyl.

The unsaturated trans-epoxide used as starting material, for example that of the above-defined formula II, can be manufactured especially by means of the same processes that are used in the synthesis of leucotrienes. For example, in a typical general method of synthesis, a saturated aliphatic aldehyde (alkanal) of the formula

$$O=CH-(CH_2)_2-R^1 \qquad (IV)$$

is used as starting material, in which $R^1$ has the meanings given above, wherein a free hydroxy group that may be present in the radical $R^1$ is present in protected form as an ether, for example one of the forms described above. This compound is condensed with formylmethylenetriphenylphosphorane (or an equivalent reagent), resulting in the corresponding α,β-unsaturated aldehyde, 2-trans-alkenal, of the formula

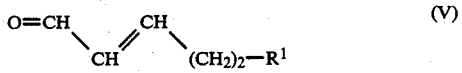

(V)

in which $R^1$ has the meanings given above and a free hydroxy group that may be present in the radical $R^1$ is protected as an ether. This compound is then, in a manner known per se, epoxidised preferably under weakly alkaline conditions, (for example in the presence of alkali carbonates) with aqueous hydrogen peroxide, resulting in a trans-epoxide, 2-(RS),3-(SR)-epoxy-alkanal of the formula

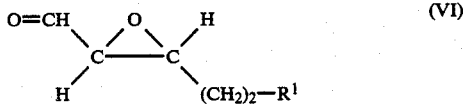

(VI)

in which $R^1$ has the meanings given above and a free hydroxy group that may be present in the radical $R^1$ is protected as an ether. This epoxyaldehyde can be condensed to the desired unsaturated epoxide, for example to that of the above-defined formula II in which a free hydroxy group that may be present in the radical $R^1$ is in protected etherified form, by condensation with a corresponding known alkylidenetriphenylphosphorane. For polyunsaturated epoxides, for example those of the formula II in which $R^2$ has one or more double bonds, there is an indirect alternative: instead of the Wittig reaction with an ylidenephosphorane unsaturated in its chain, the epoxyaldehyde VI is first, with formylmethylenetriphenylphosphorane or γ-triphenylphosphoranylidenecrotonaldehyde (4-triphenylphosphoranylidene-2-trans-butenal), lengthened by 2 or 4 carbon atoms, respectively (1 or 2 double bonds, respectively), and only the resulting 4(RS),5(RS)-epoxy-2-alkenal or 6(RS),7(RS)-epoxy-2,4-alkadienal, respectively, is condensed with a single saturated alkylidenetriphenylphosphorane or a less complicated alkenylidenetriphenylphosphorane to the desired polyunsaturated epoxide (for example one of the formula II).

If individual diastereoisomers are desired, then advantageously, at any stage, an individual diastereoisomer of a starting material can be used or a diastereoisomer can preferably be formed from a racemic or optionally inactive starting material by stereoselective reaction conditions or optionally active reagents, or racemic diastereoisomeric mixtures can be separated by physical separation methods, optionally with the use of optically active auxiliaries, into optically individual diastereoisomers.

From the stereochemical point of view, however, both the condensation according to the invention of the formation components II and III, and the preparation of the starting materials, are especially carried out using in each case stereochemically uniform starting materials, carrying out the reactions as far as possible stereoselectively, for example by using optically active reagents and/or auxiliaries, and isolating stereochemically uniform products from the reaction mixtures directly after the reaction. Thus, for example, in the manufacture of the unsaturated starting materials, isomers with cis- and trans- double bonds that may be formed are immediately separated from one another, for which purpose the customary physical separation methods, such as, especially, chromatography, are suitable. In the main reaction especially the epoxide of the formula II is used as an individual trans-stereoisomer, but in racemic form (which is the form normally obtained by the epoxidation of an olefin); the mercaptoalkanoic acid of the formula III, if it is optically active, is preferably used in the form of an individual optical antipode (which is the usual case especially with cysteine and its derivatives) - this measure makes it possible for the two optically active diastereoisomers formed to be separated from one another simply by customary physical methods, such as chromatography: if an optically inactive mercaptoalkanoic acid is used, in order to obtain individual optically active products it is absolutely necessary to use the methods of cleaving into antipodes by means of optically active auxiliaries, such as, for example, the formation of salts with optically active bases. All suitable separation processes are known per se and can also be repeated or expediently combined with each other.

Owing to the close relationship between the novel compounds in free form and in the form of their salts, there are accordingly to be understood hereinbefore and hereinafter by the free compounds or their salts also the corresponding salts and free compounds, respectively.

The invention relates also to those embodiments of the process according to which a compound obtainable as intermediate at any stage of the process is used as starting material and the remaining steps are carried out, or a starting material is used in the form of a salt or is formed under the reaction conditions.

The invention relates also to the novel starting materials and intermediates produced in the processes according to the invention and the initial stages thereof.

The starting materials and the reaction conditions are preferably so selected that the compounds listed hereinbefore as being especially preferred are obtained.

The present invention relates also to pharmaceutical compositions and medicaments that contain one of the compounds of the formula I according to the invention or a pharmaceutically acceptable salt thereof. The pharmaceutical compositions according to the invention are especially those which are designed for local administration and, especially, for inhalation administration, for example in the form of an aerosol, a micropulverised powder or a finely sprayed solution, to mammals and which contain the active ingredient on its own or together with a pharmaceutically acceptable carrier.

Pharmaceutical preparations for topical and local use are, for example for the treatment of skin, lotions and creams that contain a liquid or semi-solid oil-in-water or water-in-oil emulsion, and ointments (these preferably containing a preservative). Suitable preparations for treatment of the eyes are eyedrops that contain the active compound in aqueous or oily solution, and eye ointments that are preferably manufactured in sterile form. Suitable preparations for the treatment of the nose are aerosols and sprays (similar to those described hereinafter for the treatment of the respiratory tract), coarse powders that are administered by rapid inhalation through the nostrils and, especially, nose drops that contain the active compound in aqueous or oily solution: suitable preparations for local treatment of the buccal cavity include lozenges that contain the active compound in a composition formed generally from sugar and gum arabic or tragacanth to which flavourings can be added, and pastilles that contain the active ingredient in an inert composition, for example consisting of gelatine and glycerine or sugar and gum arabic.

Suitable pharmaceutical compositions for administration in the form of aerosols or sprays are, for example, solutions, suspensions or emulsions of the active ingredient of the formula I according to the invention with a suitable pharmaceutically acceptable solvent, such as, especially, ethanol and water, or a mixture of such solvents. Depending on the requirements the compositions can also contain other pharmaceutical adjuncts, such as non-ionic or anionic surfactants, emulsifiers and stabilisers, as well as active ingredients of other kinds, and especially advantageously can be mixed with a propellant gas, such as an inert gas under elevated pressure, or, especially, with a readily volatile liquid that preferably boils under normal atmospheric pressure below the usual room temperature (for example between approximately −30° and +10° C.), such as an at least partially fluorinated polyhalogenated lower alkane, or with a mixture of such liquids. Such pharmaceutical compositions, which are predominantly used as intermediates or as stock mixtures for the manufacture of the corresponding medicaments in finished form, contain the active ingredient usually in a concentration of from approximately 0.1 to approximately 10, especially from approximately 0.3 to approximately 3, % by weight. For the manufacture of medicaments in finished form, such a pharmaceutical composition is introduced into suitable containers, such as small bottles and pressurised bottles, which are provided with a spraying device or valve suitable for such purposes. The valve is preferably constructed as a metering valve which, on operation, releases a predetermined amount of liquid corresponding to a predetermined dose of the active ingredient. When manufacturing the finished medicament form, it is also possible for corresponding amounts of the pharmaceutical compositions present as stock solution, and of the propellant, to be introduced separately into the containers and to be mixed only then. The dosage of the active ingredient of the formula I to be administered and the frequency of administration depend on the particular activity and on the duration of action of the individual compounds, on the severity of the illness to be treated and its symptoms, and on the sex, age, weight and individual responsiveness of the mammal to be treated. On average, the recommended daily dosage of a compound of the formula I according to the invention for a mammal weighing 75 kg (especially man) is likely to lie within the range of from approximately 10 to approximately 500 mg, preferably from approximately 25 to approximately 250 mg, administration advantageously being effected in several doses per day as required.

The invention relates also to the use of the active ingredients of the formula I according to the invention for alleviating or curing pathological conditions and/or symptoms of the body of a mammal, especially man, that are attributable to the allergogenic action of leucotrienes and occur especially in the case of asthma. This use and the corresponding method of treatment is characterised by treating the affected body or part of the body with an antiallergically effective amount of a compound of the formula I on its own or in the form of a medicament, especially a pharmaceutical composition designed for inhalation. There is to be understood by "an antiallergically effective amount" that amount of the active ingredient which is sufficient to bring about significant inhibition of the contractions caused by leucotrienes.

The following Examples illustrate the present invention in more detail without limiting the scope thereof. All temperatures are quoted in degrees Celsius. The amino acids as formation components of the described compounds are in the "natural" L-form.

EXAMPLE 1

N-{S-[5(S,R),6(R,S)-5-hydroxy-7-trans,9-trans,11-cis,14-cis-icosatetraen-6-yl]-N-trifluoroacetylcysteinyl}-glycine-methyl ester and the individual 5(S),6(R)- and 5(R),6(S)-diastereoisomers A solution of 103 mg (0.36 mmol) of 5(S,R), 6(S,R)-5,6-epoxy-7-trans,9-trans,11-cis, 14-cis-icosatetraene, 154 mg (0.54 mmol) of N-(N'- trifluoroacetylcysteinyl)-glycine-methyl ester and 145 mg (1.44 mmol) of triethylamine in 0.5 ml of methanol is stirred for 4 hours at room temperature in an argon atmosphere and diluted with 2 ml of methanol. Reverse phase chromatography in the system acetonitrile/water (2:1) yields 212 mg (100%) of a diastereoisomeric mixture, which is separated into approximately equal portions of the two diastereoisomers by subsequent high pressure chromatography on a Zorbax ODS RP column with methanol/water (85:15). Under these conditions the 5(S),6(R)-diasteroisomer has a shorter retention time than the 5(R),6(S)-diastereoisomer.

UV (in methanol):
5(S),6(R)-isomer:$\lambda_{max}$=271, 281, 290 nm ($\epsilon_{281}$=40 600 ) 5(R),6(S)-iomer:$\lambda_{max}$=271, 280, 290 nm IR (CH$_2$Cl$_2$) is practically identical for both diastereoiomers: 3570 (broad), 3370 (broad), 3000, 2950, 2920, 2850, 1742, 1720, 1680, 1518, 1460, 1435, 1380–1350, 1208, 1165, 1000 cm$^{-1}$. $[\alpha]_d^{20}$ [5(S),6(R)-isomer]: +59°±1°(1.4% in CHCl$_3$).

The racemic 5(S,R),6(S,R)-5,6-epoxy-7-trans, 9-trans,11-cis,14-cis-isosatetraene used as starting material can be manufactured in the following manner:

A solution of 51.4 ml of pentanal and 147 g of triphenylphosphoranylidene acetaldehyde in 480 ml of chloroform is heated under reflux for 5 days, the solvent is distilled off under reduced pressure and the resulting residue is stirred with 400 ml of a 3:1 mixture of hexane and ether. The crystalline triphenylphosphine oxide that separates out is filtered off with suction, the filtrate is concentrated by evaporation in vacuo and the residue is distilled in vacuo, 24.5 g (45.2%) of 2-trans-heptenal are obtained in the form of a colourless oil, b.p. 60°–65° C./24 mbar.

2.04 ml of 30% strength aqueous $H_2O_2$ solution, followed by 100 mg of solid potassium carbonate, are added to a solution of 2.24 g of 2-trans-heptenal in 24 ml of methylene chloride and 44 ml of methanol at 0° C. while stirring. The resulting reaction mixture is further stirred for 3 hours at 0° C. Finally, 100 ml of methylene chloride are added and the whole is washed twice with 25 ml of phosphate buffer of pH 8.0 each time. The aqueous portions are subsequently extracted with 50 ml of methylene chloride. The combined organic portions are dried over magnesium sulphate and concentrated by evaporation under reduced pressure. Chromatography of the resulting crude product on 85 g of Merck silica gel 60 with methylene chloride as eluant yields a total of 1.59 g (62%) of 2(R,S),3(S,R)-2,3-epoxyheptanal in the form of a colourless oil. [$R_f$ (silica gel; toluene/ethyl acetate 4:1): 0.59; IR ($CH_2Cl_2$) 2950, 2925, 2850, 2820, 1721, 1463, 1430, 1378, 1210, 850 cm$^{-1}$].

A solution of 1.65 g of γ-triphenylphosphoranylidenecrotonaldehyde in 15 ml of methylene chloride is added dropwise to a solution of 640 mg of 2(R,S), 3(S,R)-2,3-epoxyheptanal in 10 ml of methylene chloride at room temperature over a period of 1 hour, and the resulting reaction mixture is stirred for a further hour at room temperature. For working up, the reaction mixture is concentrated by evaporation under reduced pressure and the residue is chromatographed on a column of 40 g of silica gel in toluene/ethyl acetate (19:1). A cis,trans- and trans,trans-isomeric mixture is obtained which, for isomerisation, is dissolved in 5 ml of methylene chloride with a few crystals of iodine and left to stand for 4 hours at room temperature. The solution is then concentrated by evaporation in vacuo and chromatographed in the manner mentioned above. 511 mg (57 %) of 6(S,R), 7(S,R)-6,7-epoxy-2-trans,4-transundecadienal are obtained in the form of a yellowish oil. [UV(ethanol): $\lambda_{max}$=276 nm; $\epsilon$=29900; IR ($CH_2Cl_2$) 2950, 2920, 2850, 2800, 2720, 1678, 1640, 1600, 1460, 1163, 1120, 1007, 985 cm$^{-1}$; $R_f$[silica gel; toluene/ethyl acetate (4:1)]=0.56.

0.31 ml of a 20% solution of butyllithium in hexane is added dropwise to a solution of 3-cis-nonen1-yl-triphenylphosphonium toluenesulphonate [I. Ernest, A. J. Main, R. Menasse, Tetrahedron Letters 23, 167 (1982)] (378 mg) in 4.2 ml of tetrahydrofuran and 1.26 ml of hexamethylphosphoric acid triamide at −78° C. under argon and the resulting solution is stirred for a further 30 minutes at −78° C. There is added dropwise to the resulting solution of triphenylphoranylidene-3-cis-nonene, at −78° C., a solution of 110 mg of 6(S,R), 7(S,R)-6,7-epoxy-2-trans,4-transundecadienal in 1.0 ml of tetrahydrofuran and the resulting reaction mixture is further stirred for 30 minutes at −78° C. For working up, the reaction mixture is partitioned between 100 ml of ether and 30 ml of phosphate buffer of pH 8.0, and the two phases are subsequently extracted again with ether and buffer solution respectively. The combined ethereal portions are dried over magnesium sulphate and concentrated by evaporation in vacuo, resulting in 421 mg of oily crude product. This is stirred with 2–3 ml of hexane/ether mixture 3:1, the crystalline triphenylphosphine oxide that separates out is removed and the filtrate is concentrated by evaporation. The resulting residue (195 mg) is chromatographed, with the same eluant, on an aluminium oxide column (10 g) prepared in hexane with 0.5 % triethylamine. 90.6 mg (57%) of 5(S,R),6(S,R)-5,6-epoxy-7-trans,9-trans,11-cis,14-cis-icosatetraene are obtained in the form of a viscous yellowish oil.

[UV (methanol): $\lambda_{max}$=270, 280, 291 nm; $\epsilon_{280}$=59 600; IR ($CH_2Cl_2$) 3000, 2900, 2850, 1455, 1370, 992, 963 cm$^{-1}$].

EXAMPLE 1A

N-{S-[5(S),6(R)-5-hydroxy-7-trans,9-trans,11-cis,14-cis-icosatetraen-6-yl]-N-trifluoroacetylcysteinyl}-glycine-methyl ester [from optically individual epoxyolefin]

A solution of 130 mg (0.450 mmol) of 5(S),6(S)-5,6-epoxy-7-trans,9-trans,11-cis,14-cis-icosatetraene, 260 mg (0.902 mmol) of N-(N-trifluoro-acetylcysteinyl)-glycine-methyl ester and 250 ml (1.8 mmol) of triethylamine in 1.0 ml of methanol is stirred for 3.5 hours at room temperature under argon and subsequently, after diluting with a small amount of methanol, chromatographed on 12 RP plates (Opti-UPC$_{12}$, ANTECH AG, Bennwil, Switzerland; 20×20 cm) in the system acetonitrile:water (1:1). The title compound (216 mg) obtained in this manner is rechromatographed on a high pressure RP column (Zorbax ODS) in methanol:water (87:13). 122 mg of pure title compound are obtained, which is identical in every respect to the diastereoisomer with the shorter retention time (see Example 1).

The optically active starting material, that is to say 5(S),6(S)-5,6-epoxy-7-trans,9-trans,11-cis, 14-cis-icosatetraene, is manufactured in the following manner:

16.9 g of 2-heptinol in 200 ml of ether are added dropwise to a solution of 10 g of lithium aluminium hydride in 400 ml of ether over a period of 30 minutes while stirring at 0° C., and the resulting reaction mixture is boiled under reflux overnight. The excess LiAlH$_4$ is destroyed while cooling in an ice-water bath by the addition of 40 ml of ethyl acetate, and the resulting reaction mixture is taken up between ether and cold 1N sulphuric acid. The acidified (pH 2) aqueous layer is subsequently extracted again with ether, and the combined organic extracts are dried over magnesium sulphate and concentrated by evaporation in vacuo. Distillation of the residue (18 g) under reduced pressure yields 13.2 g of 2-trans-heptenol in the form of a colourless oil, b.p. 71.5°–72° C./13 mbar.

A solution of 2.28 g (20 mmol) of 2-trans-heptenol in 10 ml of methylene chloride is added at −20° C. to a solution of 5.94 ml of tetraisopropyl orthotitanate and 4.12 g of L-(+)-tartaric acid diethyl ester in 210 ml of methylene chloride, followed by 9.75 ml of a 4.1M solution of tert.-butylhydroperoxide in 1,2-dichloroethane. The resulting reaction mixture is left to stand overnight at −20° C. After the addition of 8 ml of dimethyl sulphide, stirring is carried out at from −20° to −23° C. for 45 minutes, then 50 ml of a 10% strength aqueous solution of L-(+)-tartaric acid are added and the whole is further stirred for 30 minutes at −20° C. and for 60 minutes without cooling. The organic phase is separated off, subsequently washed with 100 ml of water and, after drying over magnesium sulphate, is concentrated by evaporation under reduced pressure. The residue, dissolved in 150 ml of ether, is stirred at 0° C. with 60 ml of 1N NaOH for 30 minutes, the aqueous phase is separated off and subsequently extracted with ether, and the combined organic extracts are shaken with sodium chloride solution. After drying the organic portion over magnesium sulphate and distilling off the solvent in vacuo, 2.3 g of 2(S),3(S)-2,3-epoxyheptanol are obtained in the form of a colourless unstable oil. It is immediately further processed.

A solution of 1.2 g of 2(S),3(S)-2,3-epoxy-heptanol in 28 ml of methylene chloride is added at room temperature to a freshly prepared solution of 5.5 g of chromium trioxide and 8.76 g of pyridine in 70 ml of methylene chloride and the resulting reaction mixture is further stirred for 30 minutes. The dark-coloured reaction mixture is decanted from the precipitated material which is subsequently washed with 160 ml of methylene chloride, and the combined organic portions are washed with 80 ml of phosphate buffer of pH 8.0. After drying over magnesium sulphate and concentrating by evaporation under reduced pressure, the crude product that remains is chromatographed on 90 g of Merck silica gel 60 with toluene/ethyl acetate (4:1). 464 mg of 2(R),3(S)-2,3-epoxyheptanal are obtained in the form of a colourless oil.

$[\alpha]_D^{20} = +101° \pm -1°$ (1.225% in $CHCl_3$); IR ($CH_2Cl_2$): 2950, 2925, 2860, 2815, 2730, 1722, 1462, 1432, 1380, 1360, 1230, 1156, 850 cm$^{-1}$].

A solution of 260 mg of 2(R),3(S)-2,3-epoxyheptanal in 10 ml of methylene chloride is added dropwise over a period of 1 hour at room temperature to a solution of 804 mg of γ-triphenylphosphoranylidene crotonaldehyde in 10 ml of methylene chloride, and the resulting reaction mixture is then further stirred for 1.5 hours. The solution is then concentrated to approximately 2 ml under reduced pressure and directly chromatographed on a column of 20 g of silica gel 60 with toluene/ethyl acetate (19:1). 120 mg of a cis, trans- and trans,trans-isomeric mixture are obtained, which are dissolved in 2 ml of methylene chloride with 2 mg of iodine and left to stand at room temperature for isomerisation. After 2.5 hours, the solution is concentrated in vacuo and again chromatographed in the manner described above, resulting in 103 mg of pure optically active 6(S), 7(S)-6,7-epoxy-2-trans,4-trans-undecadienal in the form of a yellow oil that solidifies into crystals at −20° C. $[\alpha]_D^{20} = 28° \pm 1°$ (0.735% in $CHCl_3$).

By condensing 90 mg of the last-mentioned compound, dissolved in 2 ml of absolute tetrahydrofuran at −78° C., with a solution of triphenylphosphoranylidene-3-cis-nonene, which has been produced from 338 mg of the corresponding phosphonium toluenesulphonate in tetrahydrofuran/hexamethylphosphoric acid triamide by the addition of butyllithium in hexane, and working up in the manner described for the racemic product (see Example 1), 132 mg (91%) of 5(S),6(S)-5,6-epoxy-7-trans,9-trans,11-cis,14-cis-icosatetraene are obtained in the form of a yellowish oil. $[\alpha]_D^{20} = -23 \pm 1°$ (0.81% in $CHCl_3$).

EXAMPLE 1B

Potassium salt of N-{S-[5(S),6(R)-5-hydroxy-7-trans,9-trans,11-cis,14-cis-icosatetraen-6-yl]-cysteinyl}-glycine.

A solution of 276 mg of potassium carbonate in 11.5 ml of water is added to a solution of 84 mg of N-{S-[5(S),6(R)-5-hydroxy-7-trans,9-trans,11-cis,14-cis-icosatetraen-6-yl]-N-trifluoroacetylcysteinyl}-glycine-methyl ester in 3.8 ml of tetrahydrofuran and 3.8 ml of methanol, and the resulting mixture is stirred for 44 hours at room temperature under argon. Finally, the mixture is concentrated under reduced pressure to approximately 3 ml and applied to reverse phase plates. Chromatography in the system acetonitrile/water (1:1) yields 40 mg of the title compound, which is stored in 5.0 ml of ethanol at −78° C.; UV (ethanol): $\lambda_{max}=271$, 280, 290 nm; $\epsilon_{280}=48\ 600$.

EXAMPLE 1C

Potassium salt of N-{S-[5(R),6(S)-5-hydroxy-7-trans,9-trans,11-cis,14-cis-icosatetraen-6-yl]-cysteinyl}-glycine Analogously to the process described in the preceding Example 1B there are obtained from 32 mg of N-{S-[5(R),6(S)-5-hydroxy-7-trans,9-trans,11-cis,14-cis-icosatetraen-6-yl]-N-trifluoroacetylcysteinyl}-glycine-methyl ester 8.5 mg of the title compound, which is stored in ethanolic solution at −78° C.; UV (ethanol): $\lambda_{max}=270$, 280, 290 nm; $\epsilon_{280}=49\ 000$.

General process

EXAMPLE 2

N-[S-5(RS),6(SR)-5-hydroxy-7-cis-heptadecen-6-yl-N-trifluoroacetylcysteinyl]-glycine-methyl ester 0.78 ml of triethylamine is added to a solution of 480 mg of 5(RS),6(RS)-5,6-epoxy-7-cis-heptadecene (E1) and 660 mg of N-[N-trifluoroacetylcysteinyl]-glycine-methyl ester [E. J. Corey et al., Tetrahedron Lett. 1980, 3143] in 6 ml of methanol. The solution is stirred for 16 hours at room temperature under argon, the solvent is evaporated off in vacuo and the residue is purified by chromatography on silica gel with dichloromethane/ethyl acetate (85:15). The title compound is obtained in the form of a colourless oil.

IR ($CH_2Cl_2$): 3400, 2940, 2870, 1755, 1740, 1690, 1530 cm$^{-1}$. The following are obtained in analogous manner:

EXAMPLE 3

N-[S-5(RS),6(SR)-5-hydroxy-7-cis-undecen-6-yl-N-trifluoroacetylcysteinyl]-glycine methyl ester, from 67 mg of 5(RS),6(RS)-5,6-epoxy-7-cis-undecene (E2) and 486 mg of N-[N-trifluoroacetylcysteinyl)-glycine-methyl ester.

IR ($CH_2Cl_2$): 3400, 2960, 2940, 2880, 1750, 1730, 1640, 1525 cm$^{-1}$.

EXAMPLE 4

N-[S-5(RS),6(SR)-5-hydroxy-7-cis-tridecen-6-yl-N-trifluoroacetylcysteinyl]-glycinemethyl ester, from 0.5 g of 5(RS),6(RS)-5,6-epoxy-7-cis-tridecene (E3) and 0.8 g of N-(N-trifluoroactylcysteinyl)-glycine-methyl ester.

IR ($CH_2Cl_2$): 3400, 2980, 2940, 2870, 1760, 1740, 1700, 1535 cm$^{-1}$.

EXAMPLE 5

S-5(RS),6(SR)-5-hydroxy-7-cis-tridecen-6-yl-cysteine-methyl ester, from 0.5 g of 5(RS),6(RS)-5,6-epoxy-7-cis-tridecene (E3) and 0.87 g of cysteine-methyl ester hydrochloride.

IR ($CH_2Cl_2$): 3600, 3400, 2970, 2950, 2880, 1750, 1445 cm$^{-1}$.

EXAMPLE 6

S-5(RS),6(SR)-5-hydroxy-7-cis-tridecen-6-yl-mercaptoacetic acid methyl ester, from 0.72 g of 5(RS),6(RS)-5,6-epoxy-7-cis-tridecene (E3) and 0.43 g of mercaptoacetic acid methyl ester.

IR=(CH$_2$Cl$_2$): 3600, 2980, 2940, 2880, 1745, 1475, 1445 cm$^{-1}$.

EXAMPLE 7

N-[S-5(RS),6(SR)-5-hydroxy-7-cis-pentadecen-6-yl-N-trifluoroacetylcysteinyl]-glycinemethyl ester, from 0.5 g of 5(RS),6(RS)-5,6-epoxy-7-cis-pentadecene (E4) and 0.71 g of N-(N-trifluoroacetylcysteinyl)-glycine-methyl ester.

IR (CH$_2$Cl$_2$): 3400, 2970, 2950, 2870, 1760, 1740, 1695, 1530 cm$^{-1}$.

EXAMPLE 7a

S-5(RS),6(SR)-5-hydroxy-7-cis-pentadecen-6-yl-N-trifluoroacetylcysteine-methyl ester, from 0.5 g of 5(RS),6(RS)-5,6-epoxy-7-cis-pentadecene (E4) and 0.58 g of N-trifluoroacetylcysteine-methyl ester.

EXAMPLE 8

S-5(RS),6(SR)-5-hydroxy-7-cis-pentadecen-6-yl-cysteine-methyl ester, from 0.5 g of 5(RS),6(RS)-5,6-epoxy-7-cis-pentadecene (E4) and 0.77 g of cysteine-methyl ester hydrochloride.

IR (CH$_2$Cl$_2$): 3600, 3400, 2970, 2940, 2870, 1750, 1475, 1445 cm$^{-1}$.

EXAMPLE 9

S-5(RS),6(SR)-5-hydroxy-7-cis-pentadecen-6-ylmercaptoacetic acid methyl ester, from 0.9 g of 5(RS),6(RS)-epoxy-7-cis-pentadecene (E4) and 0.47 g of 2-mercaptoacetic acid methyl ester.

IR (CH$_2$Cl$_2$): 3600, 2970, 2990, 2870, 1750, 1475, 1445 cm$^{-1}$.

EXAMPLE 10

S-5(RS),6(SR)-5-hydroxy-7-cis-heptadecen-6-ylcysteinyl-methyl ester, from 1 g of 5(RS),6(RS)-5,6-epoxy-7-cis-heptadecene (E1) and 1.4 g of cysteine-methyl ester hydrochloride.

IR (CH$_2$Cl$_2$): 3600, 3400, 2940, 2870, 1750, 1475 cm$^{-1}$.

EXAMPLE 11

N-[S-5(RS),6(SR)-5-hydroxy-7-cis-icosen-6-yl-N-trifluoroacetylcysteinyl]-glycine-methyl ester, from 1 g of 5(RS),6(RS)-S,6-epoxy-7-cis-icosene (E5) and 1 g of N-(N-trifluoroacetylcysteinyl)-glycine-methyl ester.

IR (CH$_2$Cl$_2$): 3400, 2930, 2860, 1750, 1735, 1690, 1530 cm$^{-1}$.

EXAMPLE 12

N-[S-5(RS),6(SR)-5-hydroxy-7-cis-tricosen-6-yl-N-trifluoroacetylcysteinyl]-glycine-methyl ester, from 0.6 g of 5(RS),6(RS)-5,6-epoxy-7-cis-tricosene (E6) and 0.58 g of N-(N-trifluoroacetylcysteinyl)-glycine-methyl ester.

IR (CH$_2$Cl$_2$): 3400, 2940, 2870, 17560, 1740, 1700, 1530 cm$^{-1}$.

EXAMPLE 13

N-{3-[4(RS),5(SR)-4-hydroxy-6-cis-tetradecen-5-ylthio]-propionyl}-glycine-methyl ester, from 300 mg of 4(RS),5(RS)-4,5-epoxy-6-cistetradecene (E7) and 275 mg of N-(3-mercaptopropionyl)-glycine-methyl ester [S. Okuyama et al, Chem. Pharm. Bull. 30, 2453 (1982)].

IR (CH$_2$Cl$_2$): 3450, 2970, 2940, 2870, 1760, 1690, 1525 cm$^{-1}$.

EXAMPLE 14

N-[S-4 (RS),5(SR)-4-hydroxy-6-cis-tetradecen-5-yl-N-trifluoroacetylcysteinyl]-glycinemethyl ester, from 0.7 g of 4(RS),5(RS)-4,5-epoxy-6-cis-tetradecene (E7) and 1.2 g of N-(N-trifluoroacetyl-cysteinyl)-glycine-methyl ester.

IR (CH$_2$Cl$_2$): 3400, 2980, 2940, 2870, 1760, 1740, 1700, 1530 cm$^{-1}$.

EXAMPLE 15

N-{3-[4(RS),5(SR)-4-hydroxy-6-cis-nonadecen-5-yl-thio]-propionyl}-glycine-methyl ester, from 250 mg of 4(RS),5(RS)-4,5-epoxy-6-cisnonadecene (E8) and 175 mg of N-(3-mercaptopropionyl)-glycine-methyl ester.

IR=(CH$_2$Cl$_2$): 3450, 2980, 2940, 2870, 1760, 1690, 1530 cm$^{-1}$.

EXAMPLE 16

N-[S-4(RS),5(SR)-4-hydroxy-6-cis-nonadecen-5-yl-N-trifluoroacetylcysteinyl]-glycine-methyl ester, from 500 mg of 4(RS),5(RS)-4,5-epoxy-6-cis-nonadecene (E8) and 620 mg of N-(N-trifluoroacetyl-cysteinyl)-glycine-methyl ester.

IR (CH$_2$Cl$_2$): 3400, 2970, 2940, 2870, 1760, 1740, 1700, 1530 cm$^{-1}$.

EXAMPLE 17

N-[S-4(RS),5(SR)-4-hydroxy-6-cis-fluoroacetylcysteinyl]-glycine-methyl ester, from 680 mg of 4(RS),5(RS)-4,5-epoxy-6-cis-icosene (E9) and 830 mg of N-(N-trifluoroacetyl-cysteinyl)-glycine-methyl ester.

IR (CH$_2$Cl$_2$): 3400, 2940, 2870, 1760, 1740, 1700, 1530 cm$^{-1}$.

EXAMPLE 17a

N-{3-[4(RS),5(SR)-4-hydroxy-6-cis-icosen-[5-yl-thio]-propionyl}-glycine-methyl ester, from 680 mg of 4(RS),5(RS)-4,5-epoxy-6-cisicosene (E9) and 720 g of N-(8-mercaptopropionyl)glycine-methyl ester.

EXAMPLE 17b

S-[4-(RS),5(SR)-4-hydroxy-6-cis-icosen-5-yl]-N-trifluoroacetylcysteine-methyl ester, from 680 mg of 4(RS),5(RS)-4,5-epoxy-6-cis-icosene (E9) and 620 mg of N-trifluoroacetylcysteine-methyl ester.

EXAMPLE 18

N-[S-6(RS),7(SR)-6-hydroxy-8-cis-icosen-7-yl-N-trifluoroacetylcysteinyl]-glycine-methyl ester, from 0.54 g of 6(RS),7(RS)-6,7-epoxy-8-cis-icosene (E10) and 0.53 g of N-(N-trifluoroacetyl-cysteinyl)-glycine-methyl ester.

IR (CH$_2$Cl$_2$): 3400, 2940, 2870, 1760, 1740, 1700, 1530 cm$^{-1}$.

EXAMPLE 18a

N-{2-[6(RS),7(SR)-6-hydroxy-8-cis-icosen-7-yl-thio]-propionyl}-glycine, from 0.54 g of 6(RS),7(RS)-6,7-epoxy-8-cis-icosene (E10) and 0.45 g of N-(α-mercaptopropionyl)glycine.

EXAMPLE 18b

S-[6(RS),7(SR)-6-hydroxy-8-cis-icosen-7-yl]-cysteine-methyl ester, from 0.54 g of 6(RS),7(RS)-6,7-epoxy-8-cis-icosene (E10) and 0.45 g of cysteine-methyl ester.

EXAMPLE 19

N-[S-5(RS),6(SR)-5-hydroxy-1-tetrahydropyranyloxy-7-cis-octadecen-6-yl-N-trifluoroacetylcysteinyl]-glycine-methyl ester, from 0.7 g of 5(RS),6(RS)-5,6-epoxy-1-tetrahydropyranyloxy-7-cis-octadecene (E11) and 0.6 g of N-(N-trifluoroacetylcysteinyl)-glycine-methyl ester.

IR ($CH_2Cl_2$): 3400, 2940, 2870, 1740, 1700, 1530 $cm^{-1}$.

EXAMPLE 19a

S-5(RS),6(SR)-5-hydroxy-1-tetrahydropyranyloxy-7-cis-octadecen-6-yl-mercaptoacetic acid methyl ester, from 0.7 g of 5(RS),6(RS)-5,6-epoxy-1-tetrahydropyranyloxy-7-cis-octadecene (E11) and 0.35 g of mercaptoacetic acid methyl ester.

EXAMPLE 20

N-[S-5(RS),6(SR)-5-hydroxy-1-tetrahydropyranyloxy-7-cis-icosen-6-yl-N-trifluoroacetylcysteinyl]-glycine-methyl ester, from 0.8 g of 5(RS),6(RS)-5,6-epoxy-1-tetrahydropyranyloxy-7-cis-icosene (E12) and 0.64 g of N-(N-tri-fluoroacetylcysteinyl)-glycine-methyl ester.

IR ($CH_2Cl_2$): 3400, 2940, 2860, 1760, 1740, 1700, 1530 $cm^{-1}$.

EXAMPLE 20a

S-5(RS),6(SR)-5-hydroxy-1-tetrahydropyranyloxy-7-cis-icosen-6-yl-mercaptoacetic acid methyl ester, from 0.8 g of 5(RS),6(RS)-5,6-epoxy-1-tetrahydropyranyloxy-7-cis-icosene (E12) and 0.4 g of mercaptoacetic acid methyl ester.

EXAMPLE 21

N-[S-5(RS),6(SR)-5-hydroxy-7-trans-9-cis-nonadecadien-6-yl-N-trifluoroacetylcysteinyl]-glycine-methyl ester, from 0.55 g of 5(RS),6(RS)-5,6-epoxy-7-trans-9-cis-nonadecadiene (E13) and 0.62 g of N-(N-trifluoroacetylcysteinyl)-glycine-methyl ester.

EXAMPLE 21a

N-{-3-[5(RS),6(SR)-5-hydroxy-7-trans-9-cis-nonadecadien-6-ylthio]-propionyl}-glycine-methyl ester, from 0.55 g of 5(RS),6(RS)-5,6-epoxy-7-trans-9-cis-nonadecadiene (E13) and 0.53 g of N-(3-mercaptopropionyl)-glycine-methyl ester.

EXAMPLE 21b

S-[5(RS),6(SR)-5-hydroxy-7-trans-9-cis-nonadecadien-6-yl]-cysteine-methyl ester, from 0.55 g of 5(RS),6(RS)-5,6-epoxy-7-trans-9-cis-nonadecadiene (E13) and 0.40 g of cysteine-methyl ester.

EXAMPLE 21c

S-[5-(RS),6(SR)-5-hydroxy-7-trans-9-cis-nonadecadien-6-yl]-mercaptoacetic acid methyl ester, from 0.55 g of 5(RS),6(RS)-5,6-epoxy-7-trans-9-cis-nonadecadiene (E13) and 0.32 g of mercaptoacetic acid methyl ester.

EXAMPLE 21d

S-[5(RS),6(SR)-5-hydroxy-7-trans-9-cis-nonadecadien-6-yl]-mercaptoacetic acid, from 0.55 g of 5(RS),6(RS)-5,6-epoxy-7-trans-9-cis-nonadecadiene (E3) and 0.30 g of mercaptoacetic acid.

EXAMPLE 21e

N-[S-5-hydroxy-7-trans-9-cis-icosadien-6-yl-N-trifluoroacetylcysteinyl]-glycine-methyl ester; diastereoisomers 5(R),6(S)- [A] and 5(S),6(R)- [B] (by chromatography): from 0.6 g of racemic 5(RS),6(RS)-5,6-epoxy-7-trans-9-cis-icosadiene (E13a) and 0.52 g of N-(N-trifluoroacetylcysteinyl)-glycine methyl ester, a mixture of the two diastereoisomers is obtained in a ratio of approximately 1:1, which is separated into the individual forms [A] and [B] of the title compound by chromatography on silica gel with hexane/ethyl acetate (7:3).

EXAMPLE 21f

N-[S-4(RS),5(RS)-4-hydroxy-6-trans-8-cis-nonadecadien-5-yl-N-trifluoroacetylcysteinyl]-glycine-methyl ester; from 0.6 g of 4(RS),5(RS)-epoxy-6-trans-8-cis-nonadecadiene (E13b) and 0.52 g of N-(N-trifluoroacetylcysteinyl)-glycine-methyl ester.

EXAMPLE 22

N-[S-5-hydroxy-1-tetrahydropyranyloxy-7-trans-9-cis-octadecadien-6-yl-N-trifluoroacetylcysteinyl]-glycine-methyl ester; diastereoisomers 5(R),6(S)- [A] and 5(S),6(R)- [B] (by chromatography): from 0.6 g of racemic 5(RS),6(RS)-5,6-epoxy-1-tetrahydropyranyloxy-7-trans-9-cis-octadecadiene (E14) and 0.52 g of N-(N-trifluoroacetylcysteinyl)-glycine-methyl ester a mixture of the two diastereoisomers is obtained in a ratio of approximately 1:1, which is separated into the individual forms [A] and [B] of the title compound by chromatography on silica gel with hexane/ethyl acetate [1:1]. The two compounds have a practically identical spectrum:

IR ($CH_2Cl_2$): 3400, 2940, 2870, 1760, 1740, 1695, 1530 $cm^{-1}$.

EXAMPLE 22a

S-[5(RS),6(SR)-5-hydroxy-1-tetrahydropyranyloxy-7-trans-9-cis-octadecadien-6-yl]-mercaptoacetic acid methyl ester: from 0.9 g of 5(RS),6(RS)-5,6-epoxy-1-tetrahydropyranyloxy-7-trans-9-cis-octadecadiene (E14) and 0.45 g of mercaptoacetic acid methyl ester.

EXAMPLE 23

N-[S-5-hydroxy-1-tetrahydropyranyloxy-7-trans-9-cis-icosadien-6-yl-N-trifluoroacetylcysteinyl]-glycine-methyl ester: diastereoisomers 5(R),6(S)- [A] and 5(S),6(R)- [B] (by chromatography). From 0.5 g of racemic 5(RS),6(RS)-5,6-epoxy-1-tetrahydropyranyloxy-7-trans-9-cis-icosadiene (E15) and 0.4 g of N-(N-trifluoroacetylcysteinyl)-glycinemethyl ester a mixture of the two diastereoisomers is obtained in a ratio of approximately 1:1, which is separated into the individual forms [A] and [B] of the title compound by chromatography on silica gel with hexane/ethyl acetate (1:1). The two compounds have a practically identical spectrum:

IR ($CH_2Cl_2$): 3400, 2940, 2870, 1760, 1740, 1700, 1530 $cm^{-1}$.

EXAMPLE 23a

S-[5(RS),6(SR)-5-hydroxy-1-tetrahydropyranyloxy-7-trans-9-cis-icosadien-6-yl]-mercaptoacetic acid methyl ester: from 0.91 g of 5(RS),6(RS)-5,6-epoxy-1-tetrahydropyranyloxy-7-trans-9-cis-icosadiene (E15) and 0.45 g of mercaptoacetic acid methyl ester.

EXAMPLE 24

N-[S-5(RS),6(SR)-5-hydroxy-7,9-trans-11-cis-hexadecatrien-6-yl-N-trifluoroacetylcysteinyl]-glycine-methyl ester, from 1.1 g of 5(RS),6(RS)-5,6-epoxy-7,9-trans-11-cis-hexadecatriene (E16) and 1.3 g of N-(N-trifluoroacetylcysteinyl)-glycine-methyl ester;

IR=($CH_2Cl_2$): 3400, 2980, 2950, 2880, 1740, 1700, 1530 $cm^{-1}$.

This diastereoisomeric mixture is separated into the two optically homogeneous forms by chromatography 5(S),6(R)-diastereoisomer is eluted first, followed by the 5(R),6(S)-diastereoisomer.

EXAMPLE 25

N-[S-5(RS),6(SR)-5-hydroxy-7,11-cis-9-trans-hexadecatrien-6-yl-N-trifluoroacetylcysteinyl]-glycine-methyl ester, from 0.5 g of 5(RS),6(RS)-5,6-epoxy-7,11-cis-9-trans-hexadecatriene (E17) and 0.62 g of N-(N-trifluoroacetylcysteinyl)-glycine-methyl ester;

IR ($CH_2Cl_2$): 3400, 2970, 2950, 2880, 1740, 1700, 1530 $cm^{-1}$.

This diastereoisomeric mixture is separated into the two optically homogeneous forms by chromatography on silica gel with hexane/ethyl acetate (2:1); the 5(S),6(R)-diastereoisomer is eluted first, $[\alpha]_D^{20} = +102.2 \pm 4.4$ followed by the 5(R),6S)diastereoisomer, $[\alpha]_D^{20} = -41.4 \pm 2.9$; both values are measured in chloroform solutions of concentration 0.255% (w/v) and 0.35% (w/v), respectively.

EXAMPLE 25a

N-[S-5(RS),6(SR)-5-hydroxy-7,9-trans-11-cis-octadecatrien-6-yl-N-trifluoroacetylcysteinyl]-glycine-methyl ester, from 0.5 g of 5(RS),6(RS)-5,6-epoxy-7,9-trans-11-cis-octadecatriene (E17a) and 0.62 g of N-(N-trifluoroacetylcysteinyl)-glycine-methyl ester.

EXAMPLE 26

N-[S-5(RS),6(SR)-5-hydroxy-7,9-trans-11-cis-icosatrien-6-yl-N-trifluoroacetylcysteinyl]-glycine-methyl ester, from 0.54 g of 5(RS),6(RS)-5,6-epoxy-7,9-trans-11-cis-icosatriene (E18) and 0.58 g of N-(N-trifluoroacetylcysteinyl)-glycine-methyl ester.

IR ($CH_2Cl_2$): 3400, 2970, 2940, 2870, 1760, 1740, 1700, 1530 $cm^{-1}$.

This diastereoisomeric mixture is separated into the individual optically homogeneous forms by chromatography on silica gel with hexane/ethyl acetate (3:2); in the first fractions the 5(S),6(R)diastereoisomer is eluted, followed by N-[S-5(R),6(S)-5-hydroxy-7,9-trans-11-cis-icosatrien-6-yl-N-trifluoroacetylcysteinyl]-glycine-methyl ester which, like its diastereoisomer, has spectral properties analogous to those of the diastereoisomeric mixture.

The two mentioned optically individual compounds can also be obtained from corresponding optically homogeneous 5,6-epoxides by condensation with N-(N-trifluoroacetylcysteinyl)-glycine-methyl ester in the following manner:

EXAMPLE 26A

N-[S-5(R),6(S)-5-hydroxy-7,9-trans-11-cis-icosatrien-6-yl-N-trifluoroacetylcysteinyl]-glycine-methyl ester:

2.48 g of triethylamine and 2.53 g of N-(N-trifluoroacetylcysteinyl)-glycine-methyl ester are added to a solution of 2.35 g of 5(R),6(S),-5,6-epoxy-7,9-trans-11-cis-icosatriene in 28 ml of methanol under argon and the whole is stirred for 16 hours at 20°. Volatile portions are removed in a water-jet vacuum and the residue is chromatographed on silica gel. Elution with hexane/ethyl acetate (3:2) yields the title compound in the form of a colourless oil, which is identical to the above-characterised product.

The optically active epoxide component can be manufactured using the process of Example 1A in the following manner:

Under anhydrous conditions, 25.7 g of 2-transheptenol (see Example 1A) and 140 ml of a 3.2M solution of tert.-butyl hydroperoxide in toluene are added in succession to a stirred solution of 66.3 ml of tetraisopropyl orthotitanate and 38.51 ml of D-(−)-tartaric acid diethyl ester in 1.1 litre of methylene chloride at −23° C., the whole is maintained at −20° C. for 16 hours and, at −23° C., is treated dropwise with 56 ml of 10% strength aqueous L-tartaric acid solution. After a further 30 minutes, the mixture is left to warm up to +20° C., and further stirred until the organic layer can clearly be separated. This is stirred for 1 hour with 1 litre of 1% strength aqueous sodium sulphite solution, separated off, washed with water, dried over sodium sulphate and concentrated in a waterjet vacuum. The residue is dissolved in 1.6 l of diethyl ether, cooled to 0° C., 675 ml of N-sodium hydroxide solution are added dropwise and the whole is stirred for 30 minutes at 0° C. The organic phase is separated off, washed with saturated sodium chloride solution, dried and concentrated, yielding 2(R),3(R)-2,3-epoxyheptanol in the form of a colourless unstable liquid, which is immediately processed in the next step.

A solution of 13.3 g of the last-mentioned compound in 100 ml of methylene chloride is added dropwise over a period of 30 minutes to a stirred suspension of 110.1 g of pyridinium chlorochromate and 41.9 g of sodium acetate in 500 ml of methylene chloride, the temperature being maintained at 25° C. by gently cooling. After 3 hours, the reaction mixture is diluted with 500 ml of diethyl ether and filtered through silica gel. The filtrate is washed with phosphate buffer of pH 8, dried over sodium sulphate and concentrated by evaporation. Chromatography of the residue on silica gel with a mixture of petroleum ether (b.p. 30°–45°) and diethyl ether (3:2) yields 2(S),3(R)-2,3-epoxyheptanal in the form of a colourless liquid; the product has spectral properties analogous to those of its 2(R),3(S)-antipode (see Example 1A).

A solution of 20.85 g of γ-triphenylphosphoranylidenecrotonaldehyde in 200 ml of methylene chloride is added dropwise to a solution of 6.7 g of 2(S),3(R)-2,3-epoxyheptanal in 250 ml of methylene chloride at 20° C. over a period of 1 hour, and the whole is stirred for a further hour at 20° C. The reaction mixture is diluted with 240 ml of hexane and 120 ml of ethyl acetate, filtered through silica gel and concentrated. The residue is taken up in equal volumes of hexane and ethyl acetate, stirred for 15 minutes, and again filtered through silica gel and concentrated. For the purpose of isomerisation, the resulting oily mixture of cis,trans- and trans,trans-isomers is dissolved in 200 ml of methanol, 220 mg of iodine are added and the whole is left to stand at 20° C. for 3 hours. After washing with an aqueous sodium thiosulphate solution and water and drying over sodium sulphate, the solution is concentrated and the residue is chromatographed on silica gel. Elution with hexane/ethyl acetate (4:1) yields the desired 6(R),7(R)-6,7-epoxy-2,4-trans-undecadienal in the form of a yellowish oil, $[\alpha]_D^{20} = 21.1 \pm 1.3°$ (0.75 w/v-% in chloroform), of which the spectral properties do not differ from those of the 6(S),7(S)-antipode (see Example 1A).

6.85 ml of a 1.6M solution of butyllithium in toluene are added to a stirred solution, cooled to −78° C., of 5.15 g of nonyltriphenylphosphonium bromide in 50 ml of tetrahydrofuran under argon. After 30 minutes at −78° C., the mixture is treated by the dropwise addition in succession of 15.1 g of hexamethylphosphoric acid triamide and a solution of 1.52 g of 6(R),7(R)-6,7-epoxy-2,4-trans-undecadienal in 10 ml of tetrahydrofuran, maintained at −78° C. for a further 15 minutes, and allowed to warm up to 0° C. Phosphate buffer (pH 8) is added to the reaction mixture, which is then extracted with ether. The combined ethereal extracts are stabilised with a few drops of triethylamine, dried over sodium sulphate and freed of readily volatile constituents at 20° C. in vacuo. The residue is stirred with small amounts of ether and freed, by filtration, of the solid triphenylphosphine oxide that separates out. The last portions of triphenylphosphine oxide are removed from the filtrate by filtration through a silica gel column, which has been prepared by washing out with a mixture (4:1) of ether/hexane with a 2% admixture of triethylamine. Removal of the solvents from the filtrate by distillation yields the desired 5(R),6(R)-5,6-epoxy-7,9-trans-11-cis-icosatriene in the form of faintly yellow crystals, m.p. 31°-32° C.

EXAMPLE 26b

N-[S-5(S),6(R)-5-hydroxy-7,9-trans-11-cis-icosatrien-6-yl-N-trifluoroacetylcysteinyl]-glycine-methyl ester is obtained in a manner analogous to that in Example 26A, but starting from 5(S),6(S)-5,6-epoxy-7,9-trans-11-cis-icosatriene. The title compound is identical to the product that can be obtained by chromatography of the diastereoisomeric mixture (see above).

The 5(S),6(S)-5,6-epoxy-7,9-trans-11-cis-icosatriene required as starting material can be obtained in an analogous manner to its 5(R),6(R)-antipode by reacting the 6(S),7(S)-6,7-epoxy-2,4-trans-undecadienal (see Example 1A) with a Wittig reagent prepared in situ from nonyltriphenylphosphonium bromide and butyllithium, in accordance with the process described in the last paragraph of Example 26A. The spectral properties of this compound correspond to those of the 5(R),5(R)-antipode characterised in Example 26A.

EXAMPLE 27

N-[S-5(RS),6(SR)-5-hydroxy-7,11-cis-9-trans-icosatriene-6-yl-N-trifluoroacetylcysteinyl]-glycine-methyl ester, from 0.94 g of 5(RS),6(RS)-5,6-epoxy-7,11-cis-9-trans-icosatriene (E19) and 1.0 g of N-(N-trifluoroacetylcysteinyl)-glycine-methyl ester.

IR (CH$_2$Cl$_2$): 3400, 2970, 2940, 2870, 1740, 1700, 1535 cm$^{-1}$.

The diastereoisomeric mixture can be separated into individual optically homogeneous diastereoisomers by chromatography analogously to Example 25 (eluant: hexane/ethyl acetate 7:3).

EXAMPLE 28

N-[S-5(RS),6(SR)-5-hydroxy-1-tetrahydropyranyloxy-7,9-trans-11-cis-icosatrien-6-yl-N-trifluoroacetylcysteinyl]-glycine-methyl ester, individual diastereoisomers 5(R),6(S)- [A] and 5(S),6(R)- [B].

There is obtained from 0.78 g of racemic 5(RS),6(RS)-5,6-epoxy-1-tetrahydropyranyloxy-7,9-trans-11-cis-icosatriene (E20) and 0.63 g of N-(N-trifluoroacetylcysteinyl)-glycine-methyl ester a mixture of diastereoisomers [A] and [B] in a ratio of approximately 1:1, from which individual forms of the title compound are isolated by chromatography on silica gel with hexane/ethyl acetate (1:1). The two have an analogous spectrum.

IR (CH$_2$Cl$_2$): 3400, 2940, 2870, 1740, 1695, 1530 cm$^{-1}$.

EXAMPLE 28a

N-[S-5(RS),6(SR)-1-acetoxy-5-hydroxy-7,9-trans-11-cis-icosatrien-6-yl-N-trifluoroacetylcysteinyl]-glycine-methyl ester, individual diastereoisomers 5(R),6(S)- [A] and 5(S),6(R)]- [B].

There is obtained from 0.78 g of racemic 5(RS),6(RS)-1-acetoxy-5,6-epoxy-7,9-trans-11-cis-icosatriene (E20a) and 0.63 g of N-(N-trifluoro-acetylcysteinyl)-glycine-methyl ester a mixture of diastereoisomers [A] and [B] in a ratio of approximately 1:1, from which individual forms of the title compound are isolated by chromatography on silica gel with hexane/ethyl acetate (1:1).

EXAMPLE 29

N-[S-5(RS),6(SR)-5-hydroxy-7,9-trans-11,14-cis-icosatetraen-6-yl-N-trifluoroacetylcysteinyl]-glycine-methyl ester; individual diastereoisomers 5(R),6(S)- [A] and 5(S),6(R)- [B].

There is obtained from 103 mg of racemic 5(RS),6(RS)-5,6-epoxy-7,9-trans-11,14-cis-icosatetraene (E21) and 154 mg of N-(N-trifluoroacetylcysteinyl)-glycine-methyl ester a mixture of diastereoisomers [A] and [B] in a ratio of approximately 1:1, from which individual forms of the title compound are isolated by chromatography on silica gel with hexane/ethyl acetate. The two have an analogous spectrum.

IR (CH$_2$Cl$_2$): 3360, 2920, 2850, 1740, 1720, 1680, 1520 cm$^{-1}$.

EXAMPLE 29a

S-5(RS),6(SR)-5-hydroxy-7,9-trans-11,14-cis-icosatetraen-6-yl-mercaptoacetic acid methyl ester: from 103 mg of 5(RS),6(RS)-5,6-epoxy-7,9-trans-11,14-cis-icosatetraene (E21) and 54 mg of mercaptoacetic acid methyl ester.

EXAMPLE 30

N-[S-5(RS),6(SR)-5-hydroxy-1-tetrahydropyranyloxy-7,9-trans-11,14-cis-icosatetraen-6-yl-N-trifluoroacetylcysteinyl]-glycine-methyl ester; individual diastereoisomers 5(R),6(S)- [A] and 5(S),6(R)- [B].

There is obtained from 0.5 g of racemic 5(RS),6(RS)-5,6-epoxy-1-tetrahydropyranyloxy-7,9-trans-11,14-cis-icosatetraene (E22) and 0.42 g of N-(N-trifluoroacetylcysteinyl)-glycine-methyl ester a mixture of diastereoisomers [A] and [B] in a ratio of approximately 1:1 from which individual forms of the title comoound are isolated by chromatography on silica gel with hexane/ethyl acetate (1:1). The two have an analogous spectrum.

IR (CH$_2$Cl$_2$): 3400, 2940, 2880, 1760, 1740, 1700, 1530 cm$^{-1}$.

EXAMPLE 31

N-[S-5(RS),6(SR)-1-acetoxy-5-hydroxy-7,11,14-cis-9-trans-icosatetraen-6-yl-N-trifluoroacetylcysteinyl]-glycine-methyl ester; individual diastereoisomers 5(R),6(S)- [A] and 5(S),6(R)- [B].

There is obtained from 490 mg of racemic 5(RS),6(RS)-1-acetoxy-5,6-epoxy-7,11,14-cis-9-trans-icosatetraene (E23) and 400 mg of N-(N-trifluoroacetylcysteinyl)-glycine-methyl ester a mixture of diastereoisomers [A] and [B] in a ratio of approximately 1:1 from which individual forms of the title compound are isolated by chromatography on silica gel with hexane/ethyl acetate (1:1). The two have an analogous spectrum.

IR (CH$_2$Cl$_2$): 3400, 2940, 2870, 1740, 1700, 1530 cm$^{-1}$.

Diastereoisomer [A]: $[\alpha]_D^{20} = -36.6 \pm 2°$ (0.5 w/v-% in chloroform)

Diastereoisomer [B]: $[\alpha]_D^{20} = +63.0 \pm 2°$ (0.5 w/v-% in chloroform)

Subsequent removal of the hydroxy-protecting group

EXAMPLE 32

N-[S-5(RS),6(SR)-1,5-dihydroxy-7-cis-icosen-6-yl-N-trifluoroacetylcysteinyl]-glycinemethyl ester.

A solution of 1.2 g of the 1-tetrahydropyranyl ether of the title compound (see Example 20) in 70 ml of a mixture consisting of 4 parts by volume of acetic acid, 2 of tetrahydrofuran and 1 of water is stirred for 6 hours at 45° C. The solvent is evaporated off in vacuo, the residue is extracted several times in toluene, and the extracts are concentrated in vacuo. Chromatography of the residue on silica gel with dichloromethane/hexane (15:1) yields the title compound.

IR (CH$_2$Cl$_2$): 3620, 3400, 2940, 2870, 1760, 1740, 1700, 1530, 1220, 1180 cm$^{-1}$.

EXAMPLE 33

N-[S-5(RS),6(SR)-1,5-dihydroxy-7-cis-octadecen-6-yl-N-trifluoroacetylcysteinyl]-glycine-methyl ester. By the process of Example 32, the title compound is obtained from 0.7 g of its corresponding 1-tetrahydropyranyl ether (see Example 19).

IR (CH$_2$Cl$_2$): 3620, 3400, 2940, 2870, 1760, 1740, 1700, 1535, 1220, 1180 cm$^{-1}$.

EXAMPLE 33a

S-5(RS),6(SR)-1,5-dihydroxy-7-cis-octadecen-6-yl-mercaptoacetic acid methyl ester. By the process of Example 32, the title compound is obtained from 0.7 g of its corresponding 1-tetrahydropyranyl ether (see Example 19a).

EXAMPLE 33b

S-5(RS),6(SR)-1,5-dihydroxy-7-cis-icosen-6-yl-mercaptoacetic acid methyl ester. By the process of Example 32, the title compound is obtained from 0.7 g of its corresponding 1-tetrahydropyranyl ether (see Example 19b).

EXAMPLE 34

N-[S-5(S),6(R)-1,5-dihydroxy-7-trans-9-cis-octadecadien-6-yl-N-trifluoroacetylcysteinyl]-glycine-methyl ester. By the process of Example 32, the title compound is obtained from 0.39 g of its corresponding 1-tetrahydropyranyl ether (see Example 22, diastereoisomer [B]).

IR (CH$_2$Cl$_2$): 3620, 3400, 2940, 2870, 1760, 1740, 1700, 1530, 1220, 1180 cm$^{-1}$.

EXAMPLE 35

N-[S-5(R),6(S)-1,5-dihydroxy-7-trans-9-cis-octadecadien-6-yl-N-trifluoroacetylcysteinyl]-glycine-methyl ester. By the process of Example 32, the title compound is obtained from 0.33 g of its corresponding 1-tetrahydropyranyl ether (see Example 22, diastereoisomer [A]).

IR (CH$_2$Cl$_2$) 3620, 3400, 2940, 2870, 1760, 1740, 1700, 1530, 1220, 1180 cm$^{-1}$.

EXAMPLE 35a

S-5(RS),6(SR)-1,5-dihydroxy-7-trans-9-cis-octadecadien-6-yl-mercaptoacetic acid methyl ester. By the process of Example 32, the title compound is obtained from 0.33 g of its corresponding 1-tetrahydropyranyl ether (see Example 22a).

EXAMPLE 36

N-[S-5(S),6(R)-1,5-dihydroxy-7- trans-9-cis-icosadien-6yl-N-trifluoroacetylcysteinyl]-glycine-methyl ester. By the process of Example 32, the title compound is obtained from 0.25 g of its corresponding 1-tetrahydropyranyl ether (see Example 23, diastereoisomer [B]).

IR (CH$_2$Cl$_2$): 3640, 3420, 2940, 2880, 1760, 1740, 1700, 1535, 1220, 1180 cm$^{-1}$.

EXAMPLE 37

N-[S-5(R),6(S)-1,5-dihydroxy-7- trans-9-cis-icosadien-6-yl-N-trifluoroacetylcysteinyl]-glycine-methyl ester. By the process of Example 32, the title compound is obtained from 0.24 g of its corresponding 1-tetrahydropyranyl ether (see Example 23, diastereoisomer [A]).

IR (CH$_2$Cl$_2$): 3620, 3400, 2940, 2870, 1760, 1740, 1700, 1535, 1220, 1180 cm$^{-1}$.

EXAMPLE 37a

S-5(RS),6(SR)-1,5-dihydroxy-7- trans-9-cis-icosadien-6-yl-mercaptoacetic acid methyl ester. By the process of Example 32, the title compound is obtained from 0.25 g of its corresponding 1-tetrahydropyranyl ether (see Example 23a, diastereoisomer [B]).

EXAMPLE 38

N-[S-5(S),6(R)-1,5-dihydroxy-7,9- trans-11-cis-icosatrien-6-yl-N-trifluoroacetylcysteinyl]-glycine-methyl ester. By the process of Example 32, the title compound is obtained from 0.56 g of its corresponding 1-tetrahydropyranyl ether (see Example 28, diastereoisomer [B]).

IR (CH$_2$Cl$_2$): 3620, 3400, 2940, 2860, 1760, 1740, 1695, 1535, 1220, 1180 cm$^{-1}$.

EXAMPLE 39

N-[S-5(R),6(S)-1,5-dihydroxy-7,9- trans-11-cis-icosatrien-6-yl-N-trifluoroacetylcysteinyl]-glycine-methyl ester. By the process of Example 32, the title compound is obtained from 49 mg of its corresponding 1-tetrahydropyranyl ether (see Example 28, diastereoisomer [A]).

IR (CH$_2$Cl$_2$): 3620, 3400, 2940, 2860, 1760, 1740, 1695, 1535, 1220, 1180 cm$^{-1}$.

EXAMPLE 40

N-(S-5(S),6(R)-1,5-dihydroxy-7,9-trans-11,14-cis-icosatetraen-6-yl-N-trifluoroacetylcysteinyl]-glycine-methyl ester. By the process of Example 32, the title compound is obtained from 140 mg of its corresponding 1-tetrahydropyranyl ether (see Example 30, diastereoisomer [B]).

IR (CH$_2$Cl$_2$): 3610, 3400, 2930, 2880, 1750, 1725, 1685, 1525, 1215, 1170 cm$^{-1}$.

EXAMPLE 41

N-[S-5(R),6(S)-1,5-dihydroxy-7,9- C trans-11,14-cis-icosatetraen-6-yl-N-trifluoroacetylcysteinyl]-glycine-methyl ester. By the process of Example 32, the title compound is obtained from 140 mg of its corresponding 1-tetrahydropyranyl ether (see Example 30, diastereoisomer [A]).

Subsequent hydrolysis of the terminal ester group

EXAMPLE 42

Sodium salt of N-[S-(5(RS),6(SR)5-hydroxy-7-cis-heptadecen-6-yl-N-trifluoroacetylcycteinyl)-glycine.

22 ml of 0.1N aqueous sodium hydroxide solution is added to a solution of 800 mg of the methyl ester of the title compound (see Example 2) in 70 ml of methanol and the whole is stirred for 16 hours at room temperature. The methanol is evaporated off in vacuo at 20° C., and 80 ml of acetonitrile are added to the aqueous residue. The solution is filtered through a small amount of silica gel and freed of solvent in vacuo at 20° C. The residue is extracted several times with chloroform and the extracts are concentrated in vacuo. After drying in a high vacuum the residue, consisting of the title compound, is pulverised.

IR (CH$_2$Cl$_2$) 3320, 2980, 2940, 2870, 1730, 1675, 1400 cm$^{-1}$.

EXAMPLE 43

Sodium salt of N-[S-5(RS),6(SR)-5- hydroxy-7-cis-undecen-6-yl-N-trifluoroacetylcysteinyl]-glycine.

In accordance with the process described in Example 41, the title compound is obtained from 1.74 g of the corresponding methyl ester (see Example 3).

IR (CH$_2$Cl$_2$): 3320, 2980, 2940, 2880, 1730, 1675, 1610, 1400 cm$^{-1}$.

EXAMPLE 44

Sodium salt of N-[S-5(RS),6(SR)-5- hydroxy-7-cis-tridecen-6-yl-N-trifluoroacetylcysteinyl]-glycine.

In accordance with the process described in Example 41, the title compound is obtained from 800 mg of the corresponding methyl ester (see Example 4).

IR (CH$_2$Cl$_2$): 3300, 2980, 2940, 2870, 1730, 1670, 1600, 1400 cm$^{-1}$.

EXAMPLE 45

Sodium salt of S-5(RS),6(SR)-5- hydroxy-7-cis-tridecen-6-yl-cysteine.

In accordance with the process described in Example 41 the title compound is obtained from 300 mg of the corresponding methyl ester (see Example 5).

IR (CH$_2$Cl$_2$): 2970, 2940, 2860, 1740, 1620, 1430 cm$^{-1}$.

EXAMPLE 46

Sodium salt of S-5(RS),6(SR)-5-hydroxy-7-cis-tridecen-6-yl-mercaptoacetic acid.

In accordance with the process described in Example 41, the title compound is obtained from 700 mg of the corresponding methyl ester (see Example 6).

IR (CH$_2$Cl$_2$): 3300, 2960, 2930, 2860, 1600, 1400 cm$^{-1}$.

EXAMPLE 47

Sodium salt of N-[S-5(RS),6(SR)-5-hydroxy-7-cis-pentadecen-6-yl-N-trifluoroacetylcysteinyl]-glycine.

In accordance with the process described in Example 41, the title compound is obtained from 710 mg of the corresponding methyl ester (see Example 7).

IR (CH$_2$Cl$_2$): 3300, 2970, 2940, 2860, 1730, 1670, 1610, 1400 cm$^{-1}$.

EXAMPLE 47a

Potassium salt of S-5(RS),6(SR)-5-hydroxy-7-cis-pentadecen-6-yl-N-trifluoroacetylcysteine.

In accordance with the process described in Example 41, the title compound is obtained from 710 mg of the corresponding methyl ester (see Example 7a).

EXAMPLE 48

Sodium salt of S-5(RS),6(SR)-5- hydroxy-7-cis-pentadecen-6-yl-cysteine.

In accordance with the process described in Example 41, the title compound is obtained from 250 mg of the corresponding methyl ester (see Example 8).

IR (CH$_2$Cl$_2$): 2970, 2940, 2870, 1740, 1640, 1590, 1410 cm$^{-1}$.

EXAMPLE 49

Sodium salt of S-5(RS),6(SR)-5- hydroxy-7-cis-pentadecen-6-yl-mercaptoacetic acid.

In accordance with the process described in Example 41, the title compound is obtained from 950 mg of the corresponding methyl ester (see Example 9).

IR (CH$_2$Cl$_2$): 3300, 2960, 2930, 2860, 1600, 1400 cm$^{-1}$.

EXAMPLE 50

Sodium salt of S-5(RS),6(SR)-5- hydroxy-7-cis-heptadecen-6-yl-cysteine.

In accordance with the process described in Example 41, the title compound is obtained from 500 mg of the corresponding methyl ester (see Example 10).

IR (CH$_2$Cl$_2$): 3300, 2940, 2870, 1600, 1410 cm$^{-1}$.

EXAMPLE 51

Sodium salt of N-[S-5(RS),6(SR)-5- hydroxy-7-cis-icosen-6-yl-N-trifluoroacetylcysteinyl]- glycine.

In accordance with the process described in Example 41, the title compound is obtained from 1.64 g of the corresponding methyl ester (see Example 11).

IR (CH$_2$Cl$_2$): 3300, 2930, 2860, 1730, 1670, 1600, 1400 cm$^{-1}$.

EXAMPLE 52

Sodium salt of N-[S-5(RS),6(SR)-5- hydroxy-7-cis-tricosen-6-yl-N-trifluoroacetylcysteinyl]-glycine.

In accordance with the process described in Example 41, the title compound is obtained from 950 mg of the corresponding methyl ester (see Example 12).

EXAMPLE 53

Sodium salt of N-{3-[4(RS),5(SR)-4- hydroxy-6-cis-tetradecen-5-yl-thio]-propionyl}- glycine.

In accordance with the process described in Example 41, the title compound is obtained from 200 mg of the corresponding methyl ester (see Example 13).

EXAMPLE 54

Sodium salt of N-[S-4(RS),5(SR)-4-hydroxy-6-cistetradecen-5-yl-N-trifluoroacetyl cysteinyl]-glycine.

In accordance with the process described in Example 41, the title compound is obtained from 600 mg of the corresponding methyl ester (see Example 14).

IR (CH$_2$Cl$_2$): 3300, 2980, 2940, 2870, 1720, 1660, 1610, 1560 cm$^{-1}$.

EXAMPLE 54a

Sodium salt of N-[S-4(RS),5(SR)-4-hydroxy-6-cis-nonadecen-5-yl-N-trifluoroacetylcystein]-glycine.

In accordance with the process described in Example 41, the title compound, m.p. 69°–73° C., is obtained from 600 mg of the corresponding methyl ester (see Example 16).

EXAMPLE 55

Sodium salt of N-[S-4(RS),5(SR)-4- hydroxy-6-cis-icosen-5-yl-N-trifluoroacetylcysteinyl]-glycine.

In accordance with the process described in Example 41, the title compound is obtained from 420 mg of the corresponding methyl ester (see Example 17).

EXAMPLE 55a

Sodium salt of N-{3-[4(RS),5( SR)-4-hydroxy-6-cis-icosen-5-yl-thio]-propionyl}-glycine.

In accordance with the process described in Example 41, the title compound is obtained from 420 mg of the corresponding methyl ester (see Example 17a).

EXAMPLE 55b

Sodium salt of S-4(RS),5(SR)-4- hydroxy-6-cis-icosen-5-yl-N-trifluoroacetylcysteine.

In accordance with the process described in Example 41, the title compound is obtained from 420 mg of the corresponding methyl ester (see Example 17b).

EXAMPLE 56

Sodium salt of N-[S-6(RS),7(SR)-6- hydroxy-8-cis-icosen-7-yl-N-trifluoroacetylcysteinyl]-glycine.

In accordance with the process described in Example 41, the title compound is obtained from 570 mg of the corresponding methyl ester (see Example 18).

IR (CH$_2$Cl$_2$): 3300, 2940, 2870, 1730, 1675, 1620, 1400 cm$^{-1}$.

EXAMPLE 56a

Sodium salt of S-5(RS),6(SR)-1,5dihydroxy-7-cis-octadecen-6-yl-mercaptoacetic acid.

In accordance with the process described in Example 41, the title compound is obtained from 570 mg of the corresponding methyl ester (see Example 33a).

EXAMPLE 56b

Potassium salt of N-[S-5(RS), 6(SR)-1,5-dihydroxy-7-cis-icosen-6-yl-N-trifluoroacetylcysteinyl]-glycine.

In accordance with the process described in Example 41, the title compound is obtained from 570 mg of the corresponding methyl ester (see Example 32).

EXAMPLE 56c

Sodium salt of S-5(RS),6(SR)-1,5- dihydroxy-7-cis-icosen-6-yl-mercaptoacetic acid.

In accordance with the process described in Example 41, the title compound is obtained from 570 mg of the corresponding methyl ester (see Example 33b).

EXAMPLE 57

Sodium salt of N-[S-5(RS),6(SR)-5- hydroxy-7-trans-9-cis-nonadecadien-6-yl-N-trifluoroacetylcysteinyl]-glycine.

In accordance with the process described in Example 41, the title compound is obtained from 410 mg of the corresponding methyl ester (see Example 21).

IR (CH$_2$Cl$_2$): 3300, 2940, 2860, 1730, 1670, 1610, 1400 cm$^{-1}$.

EXAMPLE 57a

Sodium salt of N-{3-[5(RS),6(SR)-5-hydroxy-7-trans-9-cis-nonadecadien-6-yl-thio]-propionyl}-glycine.

In accordance with the process described in Example 41, the title compound is obtained from 410 mg of the corresponding methyl ester (see Example 21a).

EXAMPLE 57b

Potassium salt of N-[S-5(R),6(S)-5- hydroxy-7-trans-9-cis-icosadien-6-yl-N-trifluoroacetylcysteinyl]-glycine.

In accordance with the process described in Example 41, the title compound is obtained from 410 mg of the corresponding methyl ester (see Example 21e, diastereoisomer [A]).

EXAMPLE 57c

Potassium salt of N-[S-5(S),6(R)-5-hydroxy-7-trans-9-cis-icosadien-6-yl-N-trifluoroacetylcysteinyl]-glycine.

In accordance with the process described in Example 41, the title compound is obtained from 410 mg of the corresponding methyl ester (see Example 21e, diastereoisomer [B]).

EXAMPLE 57d

Sodium salt of N-[S-4(RS),5(SR)-4- hydroxy-6-trans-8-cis-nonadecadien-5-yl-N-trifluoroacetylcysteinyl]-glycine.

In accordance with the process described in Example 41, the title compound is obtained from 410 mg of the corresponding methyl ester (see Example 21f). M.p. 52°–54° C.

EXAMPLE 57e

Sodium salt of S-5(RS),6(SR)-1,5- dihydroxy-7-trans-9-cis-octadecadien-6-yl-mercaptoacetic acid.

In accordance with the process described in Example 41, the title compound is obtained from 410 mg of the corresponding methyl ester (see Example 35a).

EXAMPLE 57f

Potassium salt of N-[S-5(S),6(R)-1,5-dihydroxy-7-trans-9-cis-icosadien-6-yl-N-trifluoroacetylcysteinyl]-glycine.

In accordance with the process described in Example 41, the title compound is obtained from 410 mg of the corresponding methyl ester (see Example 36).

EXAMPLE 57g

Potassium salt of N-[S-5(R),6(S)-1,5-dihydroxy-7-trans-9-cis-icosadien-6-yl-N-trifluoroacetylcysteinyl]-glycine.

In accordance with the process described in Example 41, the title compound is obtained from 410 mg of the corresponding methyl ester (see Example 37).

EXAMPLE 58

Sodium salt of N-[S-5(RS),6(SR)-5- hydroxy-7,9-trans-11-cis-hexadecatrien-6-yl-Ntrifluoroacetylcysteinyl]-glycine.

In accordance with the process described in Example 41, the title compound is obtained from 1.17 g of the corresponding methyl ester (see Example 24).

IR (CH$_2$Cl$_2$): 3300, 2970, 2940, 2880, 1730, 1670, 1620, 1410 cm$^{-1}$.

EXAMPLE 59

Sodium salt of N-[S-5(RS),6(SR)-5- hydroxy-7,11-cis-9-trans-hexadecatrien-6-yl-N-trifluoroacetylcysteinyl]-glycine.

In accordance with the process described in Example 41, the title compound is obtained from 730 mg of the corresponding methyl ester (see Example 25).

IR (CH$_2$Cl$_2$): 3300, 2970, 2940, 2880, 1730, 1675, 1625, 1410 cm$^{-1}$.

EXAMPLE 60

Sodium salt of N-[S-5(RS),6(SR)-5- hydroxy-7,9-trans-11-cis-icosatrien-6-yl-N-trifluoroacetylcysteinyl]-glycine.

In accordance with the process described in Example 41, the title compound is obtained from 230 mg of the corresponding methyl ester (see Example 26).

IR (CH$_2$Cl$_2$): 3350, 2960, 2930, 2860, 1720, 1675, 1540 cm$^{-1}$.

In an analogous manner, starting from corresponding optically individual diastereoisomers (see Examples 26A and 26B), optically individual products can be obtained:

EXAMPLE 60A

Sodium salt of N-[S-5(R),6(S)-5- hydroxy-7,9-trans-11-cis-icosatrien-6-yl-N-trifluoroacetylcysteinyl]-glycine:

26.8 ml of 0.2N sodium hydroxide solution are added dropwise to a solution of 3.1 g of N-[S-5(R),6(S)-5-hydroxy-7,9-trans-11-cis- icosatrien-6-yl-N-trifluoroacetylcysteinyl]-glycinemethyl ester (see Example 26A) in 50 ml of methanol under argon at from 0° to 5° C., and the whole is stirred for 20 hours at 20° C. and concentrated in vacuo at this temperature. By reversephase chromatography on adsorbent Merck RP8 with methanol/water (3:1), and distilling off the solvent in vacuo, the title compound is obtained in the form of a white amorphous powder.

EXAMPLE 60B

Sodium salt of N-[S-5(S),6(R)-5- hydroxy-7,9,trans-11-cis-icosatrien-6-yl-N-trifluoroacetylcysteinyl]-glycine.

Under the reaction conditions of Example 60A and using analogous amounts of the reactants and auxiliary chemicals, but starting from N-[S-5(S),6(R)-5- hydroxy-7,9-trans-11-cis-icosatrien-6-yl-N-trifluoroacetylcysteinyl]-glycine-methyl ester (see Example 26B), the title compound is obtained in the form of a white amorphous powder.

EXAMPLE 61

Sodium salt of N-[S-5(RS),6(SR)-5- hydroxy-7,11-cis-9-trans-icosatrien-6-yl-N-trifluoroacetylcysteinyl]-glycine.

In accordance with the process described in Example 41, the title compound is obtained from 370 mg of the corresponding methyl ester (see Example 27).

IR (CH$_2$Cl$_2$): 3300, 2960, 2430, 2860, 1720, 1660, 1620, 1400 cm$^{-1}$.

In an analogous manner, starting from corresponding optically individual diastereoisomers (see the chromatographic separation in Example 27), optically individual products, that is to say the 5(S),6(R)-diastereoisomer [A] and the 5(R),6(S)-diastereoisomer [B] can be obtained.

EXAMPLE 61a

Potassium salt of N-[S-5(S),6(R)- 1acetoxy-5-hydroxy-7,1-cis-9-trans-icosatrien-6- yl-N-trifluoroacetylcysteinyl]-glycine and potassium salt of N-[S-5(S),6(R)-1,5-dihydroxy-7,11-cis- 9-trans-icosatrien-6-yl-N-trifluoroacetylcysteinyl]- glycine.

The corresponding optically individual methyl ester 1-acetate (see Example 28) is reacted in accordance with the process described in Example 41, and the crude reaction mixture is separated by reversephase chromatography (elution with methanol/water 3:1). The diol compound is eluted first, followed by the 1- acetate.

EXAMPLE 61b

Potassium salt of N-[S-5(R),6(S)-1-acetoxy-5-hydroxy-7,11- cis-9-trans-icosatrien-6- yl-N-trifluoroacetylcysteinyl]-glycine and potassium salt of N-[S-5(R),6(S)-1,5-dihydroxy-7,11-cis- 9-trans-icosatrien-6-yl-N-trifluoroacetylcysteinyl]- glycine.

The corresponding optically individual methyl ester 1-acetate (see Example 28) is reacted in accordance with the process described in Example 41 and the crude reaction mixture is separated by reversephase chromatography (elution with methanol/water 3:1). The diol compound is eluted first, followed by the 1- acetate.

EXAMPLE 61c

Potassium salt of N-[S-5(R),6(S)- 5-hydroxy-7,9-trans-11,14-cis-icosatetraen-6-yl-N-trifluoroacetylcysteinyl]-glycine.

In accordance with the process described in Example 41, the title compound is obtained from 370 mg of the corresponding methyl ester (see Example 29, diastereoisomer [A]).

EXAMPLE 61d

Potassium salt of N-[S-5(S),6(R)- 5-hydroxy-7,9-trans-11,14-cis-icosatetraen-6-yl-N-trifluoroacetylcysteinyl]-glycine.

In accordance with the process described in Example 41, the title compound is obtained from 370 mg of the corresponding methyl ester (see Example 29, diastereoisomer [B]).

EXAMPLE 61e

Potassium salt of S-5(RS), 6(SR)-5-hydroxy-7,9-trans-11,14-cis-icosatetraen-6-yl-mercaptoacetic acid.

In accordance with the process described in Example 41, the title compound is obtained from 370 mg of the corresponding methyl ester (see Example 29a).

EXAMPLE 61f

Potassium salt of N-[S-5(S),6(R)- 1,5-dihydroxy-7,11,14-cis-9-trans-icosatetraen-6- yl-N-trifluoroacetyl-cysteinyl]-glycine.

In accordance with the process described in Example 41, the title compound is obtained from 370 mg of the corresponding methyl ester (see Example 31, diastereoisomer [B]).

EXAMPLE 61g

Potassium salt of N-[S-5(R),6(S)-1,5- dihydroxy-7,11,14-cis-9-trans-icosatetraen-6-yl-N-trifluoroacetyl-cysteinyl]-glycine.

In accordance with the process described in Example 41, the title compound is obtained from 370 mg of the corresponding methyl ester (see Example 31, diastereoisomer [A]).

Subsequent removal of the N-trifluoroacetyl group

EXAMPLE 62

Sodium salt of N-[S-5(RS),6(SR)-5-hydroxy-7-cis-heptadecen-6-yl-cysteinyl]-glycine.

A solution of 1.7 g of sodium carbonate in 15 ml of water is added to a solution of 590 mg of the $N^{cys}$-trifluoroacetyl derivative of the title compound (see Example 41) in 15 ml of methanol. The resulting suspension is stirred for 20 hours at 60° C. The reaction mixture is filtered and the filtrate is concentrated by evaporation in vacuo. The residue is dissolved in methanol/dichloromethane (1:1) and filtered again, and the filtrate is freed of solvent in vacuo. Reverse-phase chromatography of the residue on silica gel with methanol/water (3:1) yields the desired title compound.

IR ($CH_2Cl_2$): 3300, 2940, 2870, 1680, 1600, 1400 $cm^{-1}$.

EXAMPLE 63

Sodium salt of N-[S-5(RS),6(SR)-5-hydroxy-7-cis-undecen-6-yl-cysteinyl]-glycine.

The title compound is obtained in accordance with the general process described in Example 62 from 1.74 g of the corresponding N-trifluoroacetyl derivative (see Example 42).

IR ($CH_2Cl_2$): 3300, 2980, 2940, 2880, 1730, 1670, 1610, 1400 $cm^{-1}$.

EXAMPLE 64

Sodium salt of N-[S-5(RS),6(SR)-5-hydroxy-7-cis-tridecen-6-yl-cysteinyl]-glycine.

The title compound is obtained in accordance with the general process described in Example 62 from 320 mg of the corresponding N-trifluoroacetyl derivative (see Example 43).

IR ($CH_2Cl_2$): 3400, 2960, 2930, 2860, 1680, 1600, 1400 $cm^{-1}$.

EXAMPLE 65

Sodium salt of N-[S-5(RS),6(SR)-5- hydroxy-7-cis-pentadecen-6-yl-cysteinyl]-glycine.

The title compound is obtained in accordance with the general process described in Example 62 from 400 mg of the corresponding N-trifluoroacetyl derivative (see Example 46).

IR ($CH_2Cl_2$): 3380, 2960, 2930, 2860, 1650, 1600, 1400 $cm^{-1}$.

EXAMPLE 66

Sodium salt of N-(S-5(RS),6(SR)-5- hydroxy-7-cis-icosen-6-yl-cysteinyl]-glycine.

The title compound is obtained in accordance with the general process described in Example 62 from 1.64 g of the corresponding N-trifluoroacetyl derivative (see Example 50).

IR ($CH_2Cl_2$): 3300, 2930, 2860, 1730, 1670, 1600, 1400 $cm^{-1}$.

EXAMPLE 67

Sodium salt of N-[S-5(RS),6(SR)-5- hydroxy-7-cis-tricosen-6-yl-cysteinyl]-glycine.

The title compound is obtained in accordance with the general process described in Example 62 from 960 mg of the corresponding N-trifluoroacetyl derivative (see Example 51).

IR ($CH_2Cl_2$): 3250, 2940, 2870, 1680, 1600, 1400 $cm^{-1}$.

EXAMPLE 67a

Sodium salt of N-[S-4(RS),5(SR)-4- hydroxy-6-cis-nonadecen-5-yl-cysteinyl]-glycine.

The title compound is obtained in accordance with the general process described in Example 62 from 200 mg of the corresponding N-trifluoroacetyl derivative (see Example 54a; m.p. 182° C.

EXAMPLE 68

Sodium salt of N-[S-4(RS),5(SR)-4- hydroxy-6-cis-icosen-5-yl-cysteinyl]-glycine.

The title compound is obtained in accordance with the general process described in Example 62 from 200 mg of the corresponding N-trifluoroacetyl derivative (see Example 54a).

IR ($CH_2Cl_2$): 3420, 2940, 2860, 1720, 1670, 1620, 1400 $cm^{-1}$.

EXAMPLE 68a

Sodium salt of S-4(RS),5(SR)-4- hydroxy-6-cis-icosen-5-yl-cysteine.

The title compound is obtained in accordance with the general process described in Example 62 from 200 mg of the corresponding N-trifluoroacetyl derivative (see Example 55a); m.p. 153°-156° C.

EXAMPLE 68b

Potassium salt of N-[S-6(RS),7(SR)-6-hydroxy-8-cis-icosen-7-yl-cysteinyl]-glycine.

The title compound is obtained in accordance with the general process described in Example 62 from 200 mg of the corresponding N-trifluoroacetyl derivative (see Example 56).

EXAMPLE 68c

Sodium salt of S-6(RS),7(SR)-6- hydroxy-8-cis-icosen-7-yl-cysteine.

The title compound is obtained in accordance with the general process described in Example 62 from 200 mg of the corresponding N-trifluoroacetyl derivative (see Example 18b).

EXAMPLE 68d

Sodium salt of N-[S-5(RS),6(SR)-5- hydroxy-7-trans-9-cis-nonadecadien-6-yl-cysteinyl]- glycine.

The title compound is obtained in accordance with the general process described in Example 62 from 200 mg of the corresponding N-trifluoroacetyl derivative (see Example 57).

EXAMPLE 68e

Potassium salt of N-[S-5(R),6(S)-5- hydroxy-7-trans-9-cis-icosadien-6-yl-cysteinyl]- glycine.

The title compound is obtained in accordance with the general process described in Example 62 from 200 mg of the corresponding N-trifluoroacetyl derivative (see Example 57b).

EXAMPLE 68f

Potassium salt of N-[S-5(S),6(R)-5- hydroxy-7-trans-9-cis-icosadien-6-yl-cysteinyl]- glycine.

The title compound is obtained in accordance with the general process described in Example 62 from 200 mg of the corresponding N-trifluoroacetyl derivative (see Example 57c).

EXAMPLE 68g

Sodium salt of N-[S-4(RS),5(SR)-4- hydroxy-6-trans-8-cis-nonadecadien-5-yl-cysteinyl]- glycine.

The title compound is obtained in accordance with the general process described in Example 62 from 200 mg of the corresponding N-trifluoroacetyl derivative (see Example 57d); m.p. 98°–102° C.

EXAMPLE 68h

Potassium salt of N-[S-5(S),6(R)-5-hydroxy-7,9-trans-11-cis-icosatrien-6-yl-cysteinyl]- glycine.

The title compound is obtained in accordance with the general process described in Example 62 from 200 mg of the corresponding N-trifluoroacetyl derivative (see Example 60B).

EXAMPLE 68i

Potassium salt of N-[S-5(R),6(S)-5- hydroxy-7,9-trans-11-cis-icosatrien-6-yl-cysteinyl]-glycine.

The title compound is obtained in accordance with the general process described in Example 62 from 200 mg of the corresponding N-trifluoroacetyl derivative (see Example 60A).

EXAMPLE 68j

Potassium salt of N-[S-5(S),6(R)-5- hydroxy-7-cis-9-trans- 11-cis-icosatrien-6-yl-cysteinyl]-glycine.

The title compound is obtained in accordance with the general process described in Example 62 from 200 mg of the corresponding N-trifluoroacetyl derivative (see Example 61).

EXAMPLE 68k

Potassium salt of N-[S-5(R),6(S)-5- hydroxy- 7-cis-9-trans-11-cis-icosatrien-6-yl cysteinyl]-glycine.

The title compound is obtained in accordance with the general process described in Example 62 from 200 mg of the corresponding N-trifluoroacetyl derivative (see Example 61).

EXAMPLE 68l

Potassium salt of N-[S-5(S),6(R)-1, 5-dihydroxy-7,9-trans-11-cis-icosatrien-6-yl-cysteinyl]-glycine.

The title compound is obtained in accordance with the general process described in Example 62 from 200 mg of the corresponding N-trifluoroacetyl derivative (see Example 61a).

EXAMPLE 68m

Potassium salt of N-[S-5(R),6(S)-1, 5-dihydroxy-7,9-trans-11-cis-icosatrien-6-yl-cysteinyl]-glycine.

The title compound is obtained in accordance with the general process described in Example 62 from 200 mg of the corresponding N-trifluoroacetyl derivative (see Example 61b).

Subsequent simultaneous removal of the N-trifluoroacetyl group and hydrolysis of the terminal ester group.

EXAMPLE 69

Potassium salt of N-[S-5(S),6(R)-1,5-dihydroxy-7,9-trans-11,14-cis-icosatetraen-6-ylcysteinyl]-glycine.

A solution of 170 mg of potassium carbonate in 10 ml of water is added to a solution of 50 mg of the $N^{cys}$-trifluoroacetylmethyl ester of the title compound [see Example 39, diastereoisomer 5(S),6(R)]in 4 ml of methanol. The reaction solution is stirred for 3 days under argon and concentrated by evaporation in vacuo at room temperature. The residue is several times taken up in chloroform and concentrated by evaporation in vacuo. Reverse-phase chromatography on silica gel in the system methanol/water (3:1) yields the title compound.

EXAMPLE 69a

Potassium salt of N-[S-5(RS),6(SR)- 1,5-dihyroxy-7-cis-octadecen-6-yl-cysteinyl]-glycine.

The title compound is obtained in accordance with the general process described in Example 69 from 30 mg of the corresponding N-trifluoroacetylmethyl ester(see Example 33).

EXAMPLE 69b

Potassium salt of N-[S-5(RS),6(SR)-1,5-dihydroxy-7-cis-icosen-6-yl-cysteinyl]-glycine.

The title compound is obtained in accordance with the general process described in Example 69 from 30 mg of the corresponding N-trifluoroacetylmethyl ester (see Example 32).

EXAMPLE 69c

Potassium salt of N-[S-5(S),6(R)-1,5-dihydroxy-7-trans-9-cis-octadecadien-6-yl-cysteinyl]-glycine.

The title compound is obtained in accordance with the general process described in Example 69 from 30 mg of the corresponding N-trifluoroacetylmethyl ester (see Example 34).

EXAMPLE 69d

Potassium salt of N-[S-5(S),6(R)-5- hydroxy-7,9-trans-11-cis-hexadecatrien-6-yl- cysteinyl]-glycine.

The title compound is obtained in accordance with the general process described in Example 69 from 30 mg of the corresponding N-trifluoroacetylmethyl ester (see Example 24).

EXAMPLE 69e

Potassium salt of N-[S-5(R),6(S)-5- hydroxy-7,9-trans-11-cis-hexadecatrien-6-yl-cysteinyl]-glycine.

The title compound is obtained in accordance with the general process described in Example 69 from 30 mg of the corresponding N-trifluoroacetylmethyl ester (see Example 24).

EXAMPLE 69f

Potassium salt of N-[S-5(S),6(R)-5- hydroxy-7,11-cis-9-trans-hexadecadien-6-yl-cysteinyl]-glycine.

The title compound is obtained in accordance with the general process described in Example 69 from 30 mg of the corresponding N-trifluoroacetylmethyl ester (see Example 25).

EXAMPLE 69g

Potassium salt of N-[S-5(R),6(S)-5- hydroxy-7,11-cis-9-trans-hexadecadien-6-yl-cysteinyl]- glycine.

The title compound is obtained in accordance with the general process described in Example 69 from 30 mg of the corresponding N-trifluoroacetylmethyl ester (see Example 25).

EXAMPLE 70

Potassium salt of N-[S-5(R),6(S)-1,5-dihydroxy-7,9-trans-11,14-cis-icosatetraen-6- yl-cysteinyl]-glycine.

The title compound is obtained in accordance with the general process described in Example 69 from 30 mg of the corresponding N-trifluoroacetylmethyl ester (see Example 40, diastereoisomer [(5R,6(S)].

EXAMPLE 71

Potassium salt of N-[S-5(S),6(R)-5- hydroxy-7,9-trans-11,14-cis-icosatetraen-6-yl-cysteinyl]-glycine.

The title compound is obtained in accordance with the general process described in Example 69 from 33 mg of the corresponding N-trifluoroacetylmethyl ester (see Example 29, diastereoisomer [B]).

UV (CH$_3$OH): $\lambda_{max}$=280 nm ($\epsilon$=48 600).

EXAMPLE 72

Potassium salt of N-[S-5(R),6(S)-5- hydroxy-7,9-trans-11,14-cis-icosatetraen-6-yl- cysteinyl]-glycine.

The title compound is obtained in accordance with the general process described in Example 69 from 8 mg of the corresponding N-trifluoroacetylmethyl ester (see Example 29, diastereoisomer [A]).

UV (CH$_3$OH): $\lambda_{max}$=280 nm ($\epsilon$=48 600).

EXAMPLE 73

Potassium salt of N-[S-5(S),6(R)- 1,5-dihydroxy-7,11,14-cis-9-trans-icosatetraen-6- yl-cysteinyl]-glycine (simultaneous removal of 3 protecting groups).

A solution of 700 mg of potassium carbonate in 50 ml of water is added to a solution of 160 mg of N[S-5(S),6(R)-1-acetoxy-5-hydroxy-7,11,14-cis- 9-trans-icosatetraen-6-yl-N-trifluoroacetyl- cysteinyl]-glycine-methyl ester, the whole is stirred for 3 days at room temperature under argon and concentrated by evaporation in vacuo at room temperature. The residue is taken up in several portions of chloroform and the extract is concentrated by evaporation in vacuo. Filtration through silica gel in a solution in dichloromethane/methanol (1:3) yields the desired title compound.

IR (CH$_2$Cl$_2$): 3400, 2940, 1690, 1600, 1440, 1220, 1190 cm$^{-1}$.

EXAMPLE 74

Potassium salt of N-[S-5(R),6(S)-1,5-dihydroxy-,7,11,14-cis-9-trans-icosatetraen-6- yl-cysteinyl]-glycine (simultaneous removal of 3 protecting groups).

In a manner analogous to that described in the preceding Example, 160 mg of N-[S-5(R),6(S)-1- acetoxy-5-hydroxy-7,11,14-cis-9-trans-icosatetraen6-yl-N-trifluoroacetylcysteinyl]-glycine-methyl ester is hydrolysed to the title compound.

IR (CH$_2$Cl$_2$): 3420, 2940, 1685, 1615, 1420, 1220, 1190 cm$^{-1}$.

EXAMPLE 74a

Potassium salt of N-[S-5(R),6(S)- 1,5-dihydroxy-7-trans-9-cis-icosadien-6-yl-cysteinyl]-glycine (simultaneous removal of 3 protecting groups).

In a manner analogous to that described in Example 73, 160 mg of N-[S-5(R),6(S)-1-acetoxy-5-hydroxy7-trans-9-cis-icosadien-6-yl-N-trifluoroacetylcysteinyl]-glycine-methyl ester of Example 23a are hydrolysed to the title compound.

EXAMPLE 75

N-[S-5(RS),6(SR)-5-hydroxy-7-cis- heptadecen-6-yl-cysteinyl]-glycine.

A solution of 250 mg of sodium salt of the title compound (see Example 62) in 15 ml of dichloromethane is shaken intensively for 10 minutes at room temperature with 15 ml of 5% strength aqueous acetic acid. The organic phase is separated off, washed with water, dried over sodium sulphate and freed of solvent in vacuo. 220 mg of the title compound remain in the form of an amorphous residue.

IR (CH$_2$Cl$_2$): 3300, 2960, 2870, 1680, 1620, 1410 cm$^{-1}$.

Appendix

The starting materials used in Examples 2–74 can be manufactured in the following manner:

A Unsaturated aldehydes

A1 2-trans-Heptenal

A solution of 44.8 ml of valeraldehyde and 6.3 g of formylmethylenetriphenylphosphorane (S. Trippett and D.M. Walker, J. Chem. Soc. 1961, 1266) in 400 ml of tetrahydrofuran and 150 ml of chloroform is heated under reflux for 24 hours under argon. The red solution is freed of solvent at room temperature in vacuo and the residue is stirred with ether/hexane (1:1). The solid portion is filtered off and subsequently washed four times with ether/hexane (1:1). The filtrate is concentrated by evaporation in vacuo and the residue is distilled in vacuo. The title compound is obtained in the form of a colourless liquid (b.p. 55°–57° C./22 mbar). The following are obtained in an analogous manner:

A2 2-trans-Hexenal (b.p. =33° C./14 mbar) from 30.2 ml of butyraldehyde and 51 g of formylmethylenetriphenylphosphorane.

A3 2-trans-Octenal (b.p. =65°–69° C./16 mbar) from 20 g of hexanal and 42.6 g of formylmethylenetriphenylphosphorane.

A4 7-Tetrahydropyranyloxy-2-trans-heptenal (b.p. =106° C./5 mbar) from 16 g of 5-tetrahydropyranyloxypentanal [E.J. Corey et al., J. Am. Chem. Soc. 92, 6635 (1970)] and 26.1 g of formylmethylenetriphenylphosphorane.

A5 7-Acetoxy-2-trans-heptenal (oil) from 3.9 g of 5-acetoxypentanal [H.C. Brown et al., Synthesis 1980, 151] and 8.2 g of formylmethylenetriphenylphosphorane, after chromatography of the crude product on silica gel with hexane/ethyl acetate (3:1).

B. Epoxyaldehydes

B1. 2(RS),3(SR)-2,3-Epoxyheptanal 28 ml of 30% strength aqueous hydrogen peroxide and 800 mg of potassium carbonate are added to a solution of 9 g of 2-trans-heptenal (A1) in 200 ml of dichloromethane/methanol (1:1) and the whole is stirred for 6 hours at room temperature. 100 ml of phosphate buffer (pH=8) are added and the organic phase is separated off. The aqueous phase is extracted three times with 50 ml of dichloromethane each time. The combined organic phases are washed with 20 ml of phosphate buffer and dried over magnesium sulphate. The solution is filtered through a small amount of Florisil and concentrated by evaporation in vacuo. The title compound is obtained in the form of a colourless liquid.

IR (CH$_2$Cl$_2$): 2950, 2920, 2850, 1720, 1460, 850 cm$^{-1}$.

The folowing are obtained in an analogous manner:

B2. 2(RS),3(SR)-2,3-epoxyhexanal obtained in the form of an oil from 16.2 g of 2- trans-hexenal (A2).

IR (CH$_2$Cl$_2$): 2980, 2950, 2890, 1740, 1475, 860 cm$^{-1}$.

B3. 2(RS),3(SR)-2,3-Octanal obtained in the form of an oil from 9.0 g of 2-trans-octenal (A3).

IR (CH$_2$Cl$_2$): 2970, 2950, 2870, 1740, 1475, 1025 cm$^{-1}$.

B4. 2(RS),3(SR)-2,3-Epoxy-7-tetrahydropyranyloxyheptanal obtained in the form of an oil from 8.1 g of 7- tetrahydropyranyloxy-2-trans-heptenal (A4) by chromatography of the crude product on silica gel with hexane/ethyl acetate (2:1).

IR (CH$_2$Cl$_2$): 2950, 2880, 1735, 1140, 1130, 1080, 1040 cm$^{-1}$.

B5. 2(RS),3(SR)-7-Acetoxy-2,3-epoxyheptanal obtained in the form of an oil from 2.2 g of 7- acetoxy-2-trans-heptenal (A5) after chromatography of the crude product on silica gel with dichloromethane/ethyl acetate (93:7).

IR (CH$_2$Cl$_2$): 2960, 1740, 1375, 1240, 1050, 860 cm$^{-1}$.

C. Singly unsaturated epoxyaldehydes

C1. 4(RS),5(RS)-4,5-Epoxy-2-trans-nonenal

A solution of 7.4 g of 2(RS),3(SR)-epoxyheptanal (B1) and 17.6 g of formylmethylenetriphenylphosphorane in 250 ml of tetrahydrofuran and 100 ml of chloroform is heated under reflux for 1.5 hours under argon. The cooled solution is freed of solvent in vacuo at room temperature, and the residue is stirred with ether/hexane (4:1). The suspension is filtered through a small amount of silica gel and washed with ether/hexane (4:1). The filtrate is concentrated in vacuo and the residue is chromatographed on silica gel with hexane/ethyl acetate (5:1, with 1% triethylamine. The title compound is obtained in the form of a colourless oil, IR (CH$_2$Cl$_2$) 2970, 2940, 2870, 1690, 1650, 1115, 990 cm$^{-1}$.

The following are obtained in an analogous manner:

C1a. 4-(RS),5(RS)-4,5-Epoxy-2-trans-octenal obtained in the form of an oil from 2(RS),3(SR)-2,3-epoxyhexanal (B2).

C2. 4(RS),5(RS)-4,5-Epoxy-9-tetrahydropyranyloxy2-trans-nonenal obtained in the form of an oil from 2 g of 2(RS),3(SR)-2,3-epoxy-7-tetrahydropyranyloxyheptanal (B4).

IR (CH$_2$Cl$_2$) 2950, 2880, 1700, 1125, 1040 cm$^{-1}$.

C2a. 4(RS),5(RS)-9-Acetoxy-4,5-epoxy-2-transnonenal obtained in the form of an oil from 2(RS),3(SR)-7-acetoxy-2,3-epoxyheptanal (B5).

D. Doubly unsaturated epoxyaldehydes

D1. 6(RS),7(RS)-6,7-Epoxy-2,4-undecadienal: 2-trans-4-trans-isomer (D1a) and 2-trans-4-cis-isomer (D1b)

A solution of 4.6 g of 4-triphenylphosphoranylidene-2-trans-butenal [M. J. Berenguer et al., Tetrahedron Lett. 1971, 495]is added dropwise over a period of 1 hour at room temperature to a solution of 1.75 g of 2(RS),3(SR)-2,3-epoxyheptanal (B1) in 40 ml of dichloromethane under argon while stirring. Stirring is then continued for 1 hour and the solvent is evaporated off in vacuo at room temperature. The residue is stirred with ether/hexane (4:1), filtered through a small amount of silica gel and subsequently washed with ether/hexane (4:1). After evaporating off the solvent in vacuo, the residue is chromatographed on silica gel with hexane/ethyl acetate (4:1, with 1% triethylamine). There are obtained in the form of pale yellow oils approximately equal amounts of the 2-trans-4-cis- (D1b) and 2-trans-4-trans- (D1a) isomers of the title compound, which have analogous spectral maxima:

IR (CH$_2$Cl$_2$) 2950, 2920, 1680, 1640, 1110, 990 cm$^{-1}$.

The following are obtained in an analogous manner:

D2. 6(RS),7(RS)-6,7-Epoxy-11-tetrahydropyranyloxy-2,4-trans-undecadienal

From 1.4 g of 2(RS),3(SR)-2,3-epoxy-7-tetrahydropyranyloxyheptanal (B4) an isomeric mixture is obtained, to which iodine is then added in dichloromethane solution until the colour persists, and subsequently the whole is stirred for 5 hours at room temperature. After filtering through silica gel, the solvent is distilled off and the title compound is isolated in the form of an oil.

IR (CH$_2$Cl$_2$) 2960, 2880, 1690, 1650, 1580, 1120, 1040 cm$^{-1}$.

D3. 6(RS),7(RS)-11-Acetoxy-6,7-epoxy-2,4- undecadienal:

2-trans-4-trans-isomer (D3a) and 2-trans-4-cis-isomer (D3b). A mixture of the two isomers is obtained from 0.54 g of 2(RS),3(SR)-7-acetoxy-2,3-epoxyheptanal (B5) in a ratio of approximately 1:2 (D3a:D3b) and separated by chromatography.

E. Epoxyolefins of the formula II

E1. 5(RS),6(RS)-5,6-Epoxy-7-cis-heptadecene 12.2 ml of a 1.6 M solution of n-butyllithium in hexane is added dropwise to a solution, cooled to −30° C., of 9.4 g of n-decyltriphenylphosphonium bromide (C. T. Eyles and S. Trippett, J. Chem. Soc. (C) 1966, 67) in 50 ml of tetrahydrofuran while stirring under an argon atmosphere, the temperature being maintained between −25° and −30° C. The red solution is allowed to thaw to room temperature and is stirred for a further 10 minutes at that temperature. After cooling to −78° C., a solution of 2 g of 2(RS),3(SR)-2,3-epoxyheptanal (B1) in 10 ml of tetrahydrofuran is added dropwise over a period of 15 minutes. The solution is allowed to warm up to room temperature and stirred for a further hour. The solvent is evaporated off in vacuo at 40° C., and the residue is dissolved in dichloromethane. Silica gel is added to the solution (the amount added is sufficient for all the solvent to be absorbed), then a slurry is made with ether and the whole is filtered. Washing is carried out four times with ether/hexane (1:1) and the filtrate is concentrated in vacuo. The residue is purified by chromatography on silica gel with hexane/ethyl acetate (30:1, with 1% triethylamine). The title compound is obtained in the form of a colourless oil.

IR (CH$_2$Cl$_2$): 2980, 2940, 2870, 1475, 875 cm$^{-1}$.

The following are obtained in an analogous manner:

E2. 5(RS),6(RS)-5,6-Epoxy-7-cis-undecene from 1.3 g of 2(RS),3(SR)-2,3-epoxyheptanal (B1) and 5.5 g of n-butyltriphenylphosphonium bromide [R. Mechoulam and F. Sondheimer, J. Am. Chem. Soc. 80, 4386 (1958)].

IR (CH$_2$Cl$_2$): 2970, 2940, 2880, 1470, 875 cm$^{-1}$.

E3. 5(RS),6(RS)-5,6-Epoxy-7-cis-tridecene from 1.2 g of 2(RS),3(SR)-2,3-epoxyheptanal (B1) and 5 g of n-hexyltriphenylphosphonium bromide [C. F. Hauser et al., J. Org. Chem. 28, 372 (1963)].

IR (CH$_2$Cl$_2$): 2970, 2940, 2870, 1475, 875 cm$^{-1}$.

E4. 5(RS),6(RS)-5,6-Epoxy-7-cis-pentadecene from 1.25 g of 2(RS),3(SR)-2,3-epoxyheptanal (B1) and 5.6 g of n-octyltriphenylphosphonium bromide [C. T. Eyles and S. Trippett, J. Chem. Soc. (C) 1966, 67].

IR (CH$_2$Cl$_2$) 2970, 2930, 2870, 1475, 875 cm$^{-1}$.

E5. 5(RS),6(RS)-5,6-Epoxy-7-cis-icosene from 2 g of 2(RS),3(SR)-2,3-epoxyheptanal (B1) and 12.3 g of n-tridecyltriphenylphosphonium bromide [J. Gigg et al. J. Chem. Soc. 1966, 1872].

IR (CH$_2$Cl$_2$) 2970, 2940, 2860, 1475, 875 cm$^{-1}$.

E6. 5(RS),6(RS)-5,6-Epoxy-7-cis-tricosene from 1 g of 2(RS),3(SR)-2,3-epoxyheptanal (B1) and 5.5 g of n-hexadecyltriphenylphosphonium bromide [D. Jerchel and J. Kimmig, Chem. Ber. 83, 277 (1950)].

IR (CH$_2$Cl$_2$): 2970, 2935, 2870, 1470, 875 cm$^{-1}$.

E7 4(RS),5(RS)-4,5-Epoxy-6-cis-tetradecene from 2 g of 2(RS),3(SR)-2,3-epoxyhexanal (B2) and 10 g of n-octyltriphenylphosphonium bromide.

IR (CH$_2$Cl$_2$): 2990, 2960, 2880, 1480, 910 cm$^{-1}$.

E8 4(RS),5(RS)-4,5-Epoxy-6-cis-nonadecene from 1 g of 2(RS),3(SR)-2,3-epoxyhexanal (B2) and 3.6 g of n-tridecyltriphenylphosphonium bromide.

IR (CH$_2$Cl$_2$) 2980, 2940, 2870, 1475, 905 cm$^{-1}$.

E9 4(RS),5(RS)-4,5-Epoxy-6-cis-icosene from 0.58 g of 2(RS),3(SR)-2,3-epoxyhexanal (B2) and 3.8 g of n-tetradecyltriphenylphosphonium bromide [E. J. Reist and P. H. Christie, J. Org. Chem. 35, 3521 (1970)].

IR (CH$_2$Cl$_2$): 2940, 2870, 1470, 905 cm$^{-1}$.

E10 6(RS),7(RS)-Epoxy-8-cis-icosene from 1 g of 2(RS),3(SR)-2,3-epoxyoctanal (B3) and 4.1 g of n-dodecyltriphenylphosphonium bromide [D. Jerchel and J. Kimmig, Chem. Ber. 83, 277 (1950)].

IR (CH$_2$Cl$_2$) 2940, 2870, 1465, 875 cm$^{-4}$.

E11 5(RS),6(RS)-5,6-Epoxy-1-tetrahydropyranyloxy-7-cis-octadecene from 1 g of 2(RS),3(SR)-2,3-epoxy-7-tetrahydropyranyloxyheptanal (B4) and 6.6 g of n-undecyltriphenylphosphonium bromide (manufactured analogously to n-decyltriphenylphosphonium bromide).

IR (CH$_2$Cl$_2$) 2930, 2860, 1465, 1040 cm$^{-1}$.

E11a 5(RS),6(RS)-1-Acetoxy-5,6-epoxy-7-cis-octadecene under the same conditions as in the preceding Example, but from 2(RS),3(SR)-7-acetoxy-2,3-epoxyheptanal (B5) instead of the THP derivative B4:oil.

E12 5(RS),6(RS)-5,6-Epoxy-1-tetrahydropyranyloxy-7-cis-icosene from 1 g of 2(RS),3(SR)-2,3-epoxy-7-tetrahydropyranyloxyheptanal (B4) and 6.6 g of n-tridecyltriphenylphosphonium bromide.

IR (CH$_2$CL$_2$) 2930, 2860, 1465, 1040 cm$^{-1}$.

E12a 5(RS),6(RS)-1-Acetoxy-5,6-epoxy-7-cis-icosene under the same conditions as in the preceding Example, but from 2(RS),3(SR)-7-acetoxy-2,3-epoxyheptanal (B5) instead of the THP derivative B4:oil.

E13 5(RS),6(RS)-5,6-epoxy-7-trans-9-cis-nonadecadiene from 1 g of 4(RS),5(RS)-4.5-epoxy-2-trans-nonenal (C1) and 3.8 g of n-decyltriphenylphosphonium bromide.

E13a 5(RS),6(RS)-5,6-Epoxy-7-trans-9-cis-icosadiene from 1 g of 4(RS),5(RS)-4,5-epoxy-7-trans-nonenal (C1) and 3.9 g of n-undecyltriphenylphosphonium bromide:oil.

E13b 4(RS),5(RS)-4,5-Epoxy-6-trans-8-cis-nonadecadiene from 1 g of 4(RS),5(RS)-4,5-epoxy-7-trans-octenal (C1a) and 3.9 g of n-undecyltriphenylphosphonium bromide:oil.

E14 5(RS),6(RS)-5,6-Epoxy-1-tetrahydropyranyloxy-7-trans-9-cis-octadecadiene from 0.8 g of 4(RS),5(RS)-4,5-epoxy-9-tetrahydropyranyloxy-2-trans-nonenal (C2) and 2.2 g of n-nonyltriphenylphosphonium bromide [G. Ohloff et al. Helv. Chim. Acta 60, 1161 (1977)].

IR (CH$_2$Cl$_2$): 2940, 2870, 1585, 1460, 1040 cm$^{-1}$.

E14a 5(RS),6(RS)-1-Acetoxy-5,6-epoxy-7-trans-9-cis-octadecadiene under the same conditions as in the preceding Example, but from 4(RS),5(RS)-9-acetoxy-4,5-epoxy-2-trans-nonenal (C2a) instead of the THP derivative C2:oil.

E15 5(RS),6(RS)-5,6-Epoxy-1-tetrahydropyranyloxy-7-trans-9-cis-icosadiene from 0.8 g of 4(RS),5(RS)-4,5-epoxy-9-tetrahydropyranyloxy-2-trans-nonenal (C2) and 2.4 g of n-undecyltriphenylphosphonium bromide.

IR (CH$_2$Cl$_2$) 2940, 2870, 1585, 1450, 1040 cm$^{-1}$.

E15a 5(RS),6(RS)-1-Acetoxy-5,6-epoxy-7-trans-9-cis-icosadiene under the same conditions as in the preceding Example, but from 4(RS),5(RS)-9-acetoxy-4,5-epoxy-2-trans-nonenal (C2a) instead of the THP derivative C2:oil.

E16 5(RS),6(RS)-5,6-Epoxy-7,9-trans-11-cis-hexadecatriene from 0.95 g of 6(RS),7(RS)-6,7-epoxy-2,4-trans-undecadienal (D1a) and 2.8 g of n-pentyltriphenylphosphonium bromide [L. Jaenicke et al., Liebigs Ann. Chem. 1973, 1252].

IR (CH$_2$Cl$_2$): 2980, 2940, 2880, 1470, 1000, 870 cm$^{-1}$.

E17 5(RS),6(RS)-5,6-Epoxy-7,11-cis-9-trans-hexadecatriene from 0.78 g of 6(RS),7(RS)-6,7-epoxy-2-trans-4-cis-undecadienal (D1b) and 2.3 g of n-pentyltriphenylphosphonium bromide.

IR CH$_2$Cl$_2$): 2975, 2940, 2880, 1470, 1000, 870 cm$^{-1}$.

E17a 5(RS),6(RS)-5,6-Epoxy-7,9-trans-11-cis-octadecatriene under the same conditions as in the preceding Example, but from heptyltriphenylphosphonium bromide instead of the pentyl derivative:oil.

E18 5(RS),6(RS)-5,6-Epoxy-7,9-trans-11-cis-icosatriene from 0.65 g of 6(RS),7(RS)-6,7-epoxy-2,4- trans-undecadienal (D1a) and 4.65 g of n-nonyltriphenylphosphonium bromide.

E19 5(RS),6(RS)-5,6-Epoxy-7,11-cis-9-trans-icosatriene from 0.65 g of 6(RS),7(RS)-6,7-epoxy-2-trans-4-cis-undecadienal E(D1b) and 4.65 g of n-nonyltriphenylphosphonium bromide.

IR (CH$_2$Cl$_2$):

E20 5(RS),6(RS)-5,6-Epoxy-1-tetrahydropyranyloxy-7,9-trans-11-cis-icosatriene from 0.66 g of 6(RS),7(RS)-6,7-epoxy-11-tetrahydropyranyloxy-2,4-trans-undecadienal (D2) and 2.8 g of n-nonyltriphenylphosphonium bromide.

E20a 5(RS),6(RS)-1-Acetoxy-5,6-epoxy-7,9-trans-11-cis-icosatriene under the same conditions as in the preceding Example, but from 6(RS),7(RS)-11-acetoxy-6,7-epoxy-2,4-trans-undecadienal (D3a) instead of the THP derivative D2:oil.

E21 5(RS),6(RS)-5,6-Epoxy-7,9-trans-11,14-cis-icosatetraene from 125 mg of 6(RS),7(RS)-6,7-epoxy-2,4-trans-undecadienal (D1a) and 435 mg of 3-cis-nonenyltriphenylphosphonium iodide [E. J. Corey, et al., J. Am. Chem. Soc. 101, 6748 (1979)]

IR ($CH_2Cl_2$): 2910, 2840, 1450, 990 $cm^{-1}$.

E22 5(RS),6(RS)-5,6-Epoxy-1-tetrahydropyranyloxy-7,9-trans-11,14-cis-icosatetraene from 0.5 g of 6(RS),7(RS)-6,7-epoxy-11-tetrahydropyranyloxy-2,4-trans-undecadienal (D2) and 2.1 g of 3-cis-nonenyltriphenylphosphonium iodide.

E23 5(RS),6(RS)-1-Acetoxy-5,6-epoxy-7,11,14-cis-9-trans-icosatetraene from 0.3 g of 6(RS),7(RS)-11-acetoxy-6,7-epoxy-2-trans-4-cis-undecadienal (D3b) and 0.8 g of 3-cis-nonenyltriphenylphosphonium iodide.

Examples of pharmaceutical compositions and corresponding ready-for-use medicament forms.

By the term "active ingredient" there is to be understood hereinafter a compound of the formula I according to the invention, especially one that is described as a product in Examples 1–75, such as, for example, S-[5(RS),6(SR)-5-hydroxy-7-cis-pentadecen-6-yl]-cysteine-methyl ester, N-{S-[5(RS, 6(SR)-5-hydroxy-7-cis-heptadecen-6-yl]-N-trifluoroacetylcysteinyl}-glycine-methyl ester, sodium salt of N-{S-[5(RS),6(SR)-5-hydroxy-7-trans-9-cis-nonadecadien-6-yl]-N-trifluoroacetylcysteinyl}-glycine, N-{S-[5(RS),6(SR)-5-hydroxy-7,9-trans-11-cis-icosatrien-6-yl]-N-trifluoroacetylcysteinyl}-glycine-methyl ester, N-{S-[5(RS),6(SR)-5-hydroxy-7,9-trans-11,14-cis-icosatetraen-6-yl]-cysteinyl}-glycine (also in optically active form), and the potassium salt of N-{S-[5(RS),6(SR)-1,5-dihydroxy-7,9-trans-11,14-cis-icosatetraen-6-yl]-cysteinyl}-glycine (also in optically active form).

EXAMPLE A

An inhalation suspension forming a solid aerosol, containing propellant and 0.1% by weight of active ingredient.

| Composition: | % by weight |
| --- | --- |
| active ingredient, micronised | 0.1 |
| sorbitan trioleate | 0.5 |
| propellant A (trichlorotrifluoroethane) | 4.4 |
| propellant B | |
| (dichlorodifluoromethane and 1,2-dichlorotetrafluoroethane) | 15.0<br>80.0 |

Manufacture: With the aid of a customary homegeniser, the active ingredient is suspended, with the exclusion of moisture, in trichlorotrifluoroethane with the addition of sorbitan trioleate, and the suspension is introduced into an aerosel container fitted with a dosing valve; the container is sealed and filled up under pressure with propellant B.

EXAMPLE B

An approximately 2% strength aqueous solution of an active ingredient in the form of its sodium or potassium salt, suitable for inhalation.

| Composition | |
| --- | --- |
| active ingredient (K or Na salt) | 2000 mg |
| disodium salt of ethylenediaminetetraacetic acid | 10 mg |
| benzalkonium chloride | 10 mg |
| water, freshly distilled | ad 100 mg |

Manufacture: The active ingredient is dissolved in approximately 60 ml of freshly distilled water and the stabiliser (disodium salt of ethylenediaminetetraacetic acid) and preservative (benzalkonium chloride) are added. When all the components have completely dissolved, the resulting solution is made up to 100 ml and introduced into small pressurised bottles and these are sealed in gas-tight manner. The propellant is added as required, in the form of a gas under pressure or in liquid form.

APPENDIX—PHARMACOLOGICAL TEST METHODS

Bronchoconstriction test in guinea-pigs (in vivo, aerosol)

Male guinea pigs weighing from 400 to 700 g are anaesthetised intraperitoneally with 1.4 g/kg of urethane and a polyethylene tube is introduced into the jugular vein. A second polyethylene tube is introduced into the trachea. The pressure in the oesophagus is measured by means of a tube which is introduced into the oesophagus and is connected to a Statham pressure transducer. The animal is placed in a Plexiglass chamber that can be sealed in an air-tight manner and that is connected to a Fleisch tube No. 000 and a Validyne transducer MP 45-1. The flow is measured by means of this arrangement.

After surgical preparation of the experimental animals, a certain time is allowed to elapse so that the pulmonary functions can stabilise. The compound to be tested is then administered in accordance with the following protocol. The experimental animals are exposed for one minute to a 1% aerosol solution of the compound to be tested (w/v) or to distilled water (for control purposes). For all test compounds that are administered by inhalation, a Monaghan ultrasound spray device (model 670) is used of which the particle size ranges from 1 to 8 microns, the majority being 3 microns.

Aqueous solutions are each freshly prepared and introduced by means of an on-stream drug vial into the chamber of the spray device. The spray mist produced is administered to the experimental animals via a 65 ml glass chamber which is connected to the trachea by a tube. At the end of the treatment period, $LTD_4$ (0.3 μg/ml) is administered for two minutes using a second Monaghan ultrasound spray device (model 670) and via an identical glass chamber.

The reduction in the compliance in the 3rd minute after $LTD_4$ administration is read by comparing the mean value of three animals with the mean value of three control animals and the percentage inhibition of the compliance is calculated in accordance with the following formula:

$$\% \text{ inhibition} = 100 - \frac{(100 - \text{compliance preparation}) \cdot 100}{(100 - \text{compliance control})}$$

If different concentrations of active ingredient are examined, the percentage inhibition for each concentration is recorded by entering the log concentration on the abscissa against the percentage inhibition on the ordinate. The $IC_{50}$ is then ascertained by linear regression analysis.

In vitro test for determining the inhibition of phospholipase $A_2$ obtained from human leucocytes Human neutrophilic polymorphonuclear leucocytes are isolated from "buffy coats" by multistage fractional sedimentation and deep-frozen. Phospholipase $A_2$ is extracted from the cell suspension by homogenisation with the addition of icecold 0.36N $H_2SO_4$ in 2N NaCl, and the supernatant obtained after centrifugation at $10,000 \times g$ is dialysed against sodium acetate buffer pH 4.5.

In order to determine the enzyme activity, enzyme (10–30 μg protein) is incubated at 37° for 1 hour in 0.1M tris/HCl buffer pH 7 with the addition of 1 mM $CaCl_2$ and substrate consisting of phospholipides (2 μm) of *Escherichia coli* that have been radioactively labelled with $^{14}$C-oleic acid by means of biosynthesis. The reaction is stopped by the addition of Dole reagent (isopropanol/heptane/1N $H_2SO_4$ 40:10:1, v/v) and the $^{14}$C-oleic acid selectively released by phospholipase $A_2$ is extracted. Substrate also extracted at the same time is completely removed by filtering the extract through a column of silica gel. The $^{14}$C-oleic acid in the eluate is determined by radiometry.

In order to ascertain the inhibitory action of test substances on phospholipase $A_2$, these substances are added in the form of solutions in water, dimethyl sulphoxide (final concentration in the mixture up to 5% v/v) or ethanol (final concentration in the mixture up to 2.5% v/v) to the incubation mixture. The strength of action of the test substances is expressed by the $IC_{50}$, that is to say, the concentration that causes a 50% inhibition of the control activity. The $IC_{50}$ is ascertained on a graph by plotting the percentage inhibition on the ordinate against the log of the concentration (μM) on the abscissa.

Under the test conditions described, mepacrine inhibits phospholipase $A_2$ with an $IC_{50}$ of 1600 μM.

In vitro test for determining the inhibition of phospholipase C obtained from human thrombocytes Human thrombocytes are obtained from "buffy coats" by fractional centrifugation and then deep frozen. The phospholiphase C is released by ultrasound treatment of the cell suspension and, after ultracentrifugation ($150,000 \times g$ for 1 hour), is found in soluble form in the supernatant.

To ascertain the enzyme activity, enzyme (20–100 μg protein) is incubated at 37° for 5 minutes in 0.025M tris/malate buffer pH 6 with the addition of 0.2 mM $CaCl_2$ and 0.02 mM radioactively labelled substrate, phosphatidyl-[$^{14}$C]-inositol. The reaction is stopped by extraction by shaking with $CHCl_3/CH_3OH$ 2:1 (v/v). In the course of this unconsumed substrate is extracted into the organic phase, whilst the reaction product, $^{14}$C-inositol phosphate, remains in the aqueous phase and can be measured by radiometry of an aliquot.

In order to ascertain the inhibitory action of test substances on phospholipase C, these substances are added in the form of solutions in water, dimethyl sulphoxide (final concentration in the mixture up to 5%, v/v) or ethanol (final concentration in the mixture up to 2.5%, v/v) to the incubation mixture. The strength of action of the test substances is expressed by the $IC_{50}$, that is to say the concentration that causes a 50% inhibition of the control activity. The $IC_{50}$ is ascertained on a graph by plotting the percentage inhibition on the ordinate against the log of the concentration (μM) on the abscissa.

Under the test conditions described, mepacrine inhibits phospholipase C with an $IC_{50}$ of 20 μM.

We claim:

1. A compound of the formula

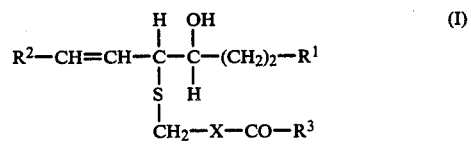

in which $R^1$ represents a $C_{1-3}$-alkyl radical or a $C_{1-3}$-alkyl radical or $C_{1-3}$-hydroalkyl which is free or esterified with a $C_1$–$C_{12}$ alkanoic acid, $R_2$ represents a saturate or unsaturated aliphatic radical having from 5 to 15 carbon atoms, $R_3$ represents hydroxy, $C_1$–$C_7$ alkoxy, an unsubstituted amino group or a substituted amino group of the formula

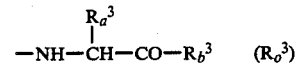

in which $R_b^3$ represents hydrogen or a $C_{1-5}$-alkyl radical and $R_b^3$ represents hydroxy, $C_{1-7}$-alkoxy or a primary amino group, —X— represents a single bond, a methylene group, a aminomethylene group or a primary aminomethylene which has been acylated with a $C_1$–$C_{12}$ carboxylic acid wherein the O-atom of the hydroxy group is in the trans-configuration relative to the S-atom, or a salt of such compound having a salt-forming property.

2. A compound according to claim 1 wherein said primary amino methylene and acylated primary aminomethylene of —X— is of the partial formula

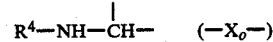

in which $R^4$ represents hydrogen, the acyl radical of a carboxylic acid or corresponding amino acid, said acyl radical having a maximum of 12 carbon atoms which carboxylic acid is unsubstituted or further substituted by halogen.

3. A compound according to claim 2, wherein, $R^1$ represents ethyl or β-hydroxyethyl, which may be esterified by an alkanoic acid having from 1 to 4 carbon atoms.

4. A compound according to claim 2, wherein $R^1$ represents ethyl, β-hydroxyethyl or β-acetoxyethyl.

5. A compound according to claim 1, wherein, $R^2$ represents a $C_{5-15}$-alkyl radical or a corresponding radical having one, two or three double bonds.

6. A comoound according to claim 5, wherein, $R^2$ represents a linear alkyl radical having from 5 to 15 carbon atoms.

7. A compound according to claim 5, wherein $R^2$ represents a linear 1-alkenyl radical having from 5 to 12 carbon atoms.

8. A compound according to claim 5, wherein, $R^2$ represents a linear 1,3-alkadienyl radical having from 5 to 12 carbon atoms.

9. A compound according to claim 5, wherein, $R^2$ represents a linear 1,3,6-alkatrienyl radical having from 8 to 12 carbon atoms.

10. A compound according to claim 1 wherein $R^1$ represents methyl, ethyl, propyl or a β-hydroxyethyl group or β-hydroxyethyl esterified by a $C_{1-4}$-alkanoic acid, $R^2$ represents a linear $C_{5-15}$-alkyl radical or a corresponding radical having from 1 to 3 double bonds, $R^3$ represents hydroxy, $C_{1-7}$-alkoxy or a radical of the partial formula $-NH-CH_2-COR_b{}^3$ (in which $R_b{}^3$ represents hydroxy or $C_{1-7}$-alkoxy) and —X— represents a single bond, a methylene group or a group of the partial formula

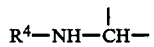

in which $R^4$ represents hydrogen or the acyl radical of a carboxylic acid having a maximum of 12 carbon atoms which is unsubstituted or substituted by halogen or an acyl radical of an alpha-amino acid, or a salt of such compound having a salt-forming property.

11. A compound according to claim 1, wherein, $R^3$ represents hydroxy or methoxy.

12. A compound according to claim 1, wherein $R^3$ represents a glycine radical bonded by its nitrogen atom or such a glycine radical esterified by a $C_{1-4}$-alkanol radical.

13. A compound according to claim 10, wherein, —X— represents a single bond or a methylene group.

14. A compound according to claim 10, wherein, —X— represents the group —$X_o$— in which $R^4$ represents hydrogen or trifluoroacetyl.

15. A compound according to claim 10, wherein, —X— represents the group —$X_o$— in which $R^4$ represents the acyl radical of a naturally occurring mono- or di-basic ε-amino acid.

16. A compound according to claim 10, wherein, —X— represents the group —$X_o$— in which $R^4$ represents the γ-glutamyl radical, or a salt form thereof.

17. A compound according to claim 30, wherein, the grouping —S—$CH_2$—X—CO—$R^3$ represents a residue, bonded by the S-atom, of mercaptoacetic acid or of its methyl ester.

18. A compound according to claim 30, wherein, the grouping S—$CH_2$—X—CO—$R^3$ represents a residue, bonded by the S-atom, of β-mercaptopropionic acid or of N-(β-mercaptopropionyl)-glycine, or of a corresponding methyl ester thereof.

19. A compound according to claim 30, wherein, the grouping —S—$CH_2$—X—CO—$R^3$ represents an L-cysteinyl or N-acylated -L-cysteinyl residue of the formula

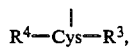

in which $R^3$ represents hydroxy or $C_{1-4}$-alkoxy and $R^4$ represents hydrogen, trifluoroacetyl or γ-glutamyl.

20. A compound according to claim 30, wherein, the grouping —S—$CH_2$—X—CO—$R^3$ represents an N-(L-cysteinyl)-glycyl residue N-acylated-N-(L-cysteinyl)-glycyl of the formula

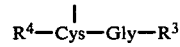

in which $R^3$ represents hydroxy or $C_{1-4}$-alkoxy and $R^4$ represents hydrogen, trifluoroacetyl or γ-glutamyl.

21. N-{S-[5(RS),6(SR)-5-Hydroxy-7,9-trans-11-cis-icosatrien-6-yl]-N-trifluoroacetylcysteinyl}-glycine in the form of the methyl ester, free acid or an alkali metal salt, as a compound according to claim 1.

22. N-{S-[5(S),6(R)-5-Hydroxy-7,9-trans-11-cis-icosatrien-6-yl]-N-trifluoroacetylcysteinyl}-glycine in the form of the methyl ester, free acid or an alkali metal salt, as a compound according to claim 1.

23. N-{S-[5(R),6(S)-5-Hydroxy-7,9-trans-11-cis-icosatrien-6-yl]-N-trifluoroacetylcysteinyl}-glycine in the form of the methyl ester, free acid or an alkali metal salt, as a compound according to claim 1.

24. N-{S-[5(RS),6(SR)-5-Hydroxy-7,9-trans-11,14-cis-icosatetraen-6-yl]-cysteinyl}-glycine in the form of the methyl ester, free acid or an,alkali metal salt, as a compound according to claim 1.

25. N-{S-[5(S),6(R)-5-Hydroxy-7,9-trans-11,14-cis-icosatetraen-6-yl]-cysteinyl}-glycine in the form of the methyl ester, free acid or an alkali metal salt, as a compound according to claim 1.

26. N-{S-[5(R),6(S)-5-Hydroxy-7,9-trans-11,14-cis-icosatetraen-6-yl]-cysteinyl}-glycine in the form of the methyl ester, free acid or an alkali, metal salt, as a compound according to claim 1.

27. N-{S-[5(RS),6(SR)-1,5-Dihydroxy-7,9-trans-11,14-cis-icosatetraen-6-yl]-cysteinyl}-glycine in the form of the methyl ester, free acid or an alkali metal salt, as a compound according to claim 1.

28. N-{S-[5(S),6(R)-1,5-Dihydroxy-7,9-trans-11,14-cis-icosatetraen-6-yl]-cysteinyl}-glycine in the form of the methyl ester, free acid or an alkali metal salt, as a compound according to claim 1.

29. N-{S-[5(R),6(S)-1,5-Dihydroxy-7,9-trans-11,14-cis-icosatetraen-6-yl]-cysteinyl}-glycine in the form of the methyl ester, free acid or an alkali metal salt, as a compound according to claim 1.

30. A pharmaceutically acceptable salt of a compound of claim 1 having at least one free carboxy group.

31. A pharmaceutical composition for the treatment of a leucotriene dependent condition comprising a leucotriene antagonistic amount of at least one compound of claim 40 and a pharmaceutically acceptable carrier.

32. The composition of claim 31 which is in a ready-for-use form.

33. The composition of claim 31 or 32 which is suitable for inhalation administration.

34. A method for the alleviation or elimination of a pathological condition or symptom attributable to the allergogenic action of a leucotriene, inflammation, or thrombosis in a mammal comprising administering to said mammal in need of such treatment and effective amount of a compound of claim 1.

35. The method of claim 34 wherein said condition is an asthmatic condition and said administration is by inhalation.

36. The method of claim 34 or 35 wherein said mammal is a human being.

* * * * *